US005858773A

United States Patent [19]

Mazodier et al.

[11] Patent Number: 5,858,773

[45] Date of Patent: Jan. 12, 1999

[54] REGULATORY NUCLEOTIDE SEQUENCE OF THE INITIATION OF TRANSCRIPTION

[75] Inventors: Philippe Mazodier, Clamart; Gerard Guglielmi, Levallois-Perret, both of France

[73] Assignee: Institut Pasteur, Paris, France

[21] Appl. No.: 461,775

[22] Filed: Jun. 5, 1995

Related U.S. Application Data

[63] Continuation of Ser. No. 50,313, filed as PCT/FR91/00701 Sep. 3, 1991 published as WO92/04452 Mar. 19, 1992, abandoned.

[30] Foreign Application Priority Data

Sep. 10, 1990 [FR] France .................................... 9011186

[51] Int. Cl.[6] .......................... C07K 14/00; C07H 21/00; C12N 1/20; C12N 15/00

[52] U.S. Cl. .................. 435/320.1; 435/69.1; 435/172.3; 435/252.3; 435/253.5; 530/350; 536/23.1; 536/24.1

[58] Field of Search ................................. 536/23.1, 24.1; 435/172.3, 252.3, 320.1, 69.1, 253.5; 530/350

[56] References Cited

U.S. PATENT DOCUMENTS 4,797,359 1/1989 Finkelstein ............................ 435/69.1

FOREIGN PATENT DOCUMENTS 0 179 449 4/1986 European Pat. Off. .
0 352 707 1/1990 European Pat. Off. .

OTHER PUBLICATIONS

*Molecular Microbiology*, "Heat-shock and General Stress Response in *Bacillus subtilis*", M. Hecker, et al., 1996, vol. 19, No. 3, pp. 417–428.

*Mol. Gen Genet*, "Transcriptional Analysis of groEL Genes of *Streptomyces coelicolor* A3(2)", A. Duchêne, et al., 1994, vol. 245, pp. 61–68.

*Molecular Biology*, "Post–Transcriptional Regulation of the groEL1 gene of *Streptomyces albus*", P. Servant, et al., (1994), 12(3), pp. 423–432.

*Journal of Bacteriology*, "Characterization of *Streptomyces albus* 18–Kilodalton Heat Shock–Responsive Protein", P. Servan et al., Jun. 1995, vol. 177, No. 11, pp. 2998–3003.

*The Journal of Antibiotics*, "Cloning of DNA Fragments Containing *Streptomyces* Promoter Activity", Taichi Manome et al, Oct. 1987, vol. XL, No. 10, pp. 1440–1447.

*Gene*, "Nucleotide Sequence of the Putative Regulatory Gene and Major Promoter Region of the *Streptomyces griseus* Glycerol Operon", Alexander Bolotin, et al, 1990, vol. 87, pp. 151–152.

*Gene*, "Two Promoters from the *Streptomyces* Plasmid PIJ101 and Their Expression in *Escherichia coli*", Mark J. Buttner, et al, vol. 51, 1987, pp. 179–186.

*Journal of General Microbiology*, "Cloning and Sequence Analysis of the 10 kDa Antigen Gene of *Mycobacterium tuberculosis*", Paul N. Baird et al, 1989, vol. 135, pp. 931–939.

*Primary Examiner*—George C. Elliott
*Assistant Examiner*—Sean M. Garry
*Attorney, Agent, or Firm*—Burns, Doane, Swecker & Mathis, L.L.P.

[57] ABSTRACT

The invention relates to a recombinant nucleotide sequence, characterized in that it comprises:

a regulatory sequence of the initiation of transcription, this regulatory sequence containing a promoter in association with the motif GCACTC 9N GAGTGC, in which "N" signifies any one of the 4 bases thymine, guanine, adenine and cytosine;

a sequence coding for a polypeptide, called "heterologous polypeptide", which is different from that naturally associated with the promoter; the coding sequence being positioned downstream from the regulatory sequence of the initiation of transcription at a site which, under suitable conditions, would allow the expression of the polypeptide under the control of the promoter.

16 Claims, 16 Drawing Sheets

P1:

CATTGGCACTCCGCTTGACCGAGTGCT AATCGCGGTCATAGTCTCAGCTCTG
5′ 3′

-30 -10 +1
GCATTGGCACTCCGCTTGACCGAGTGCTAATCGCGGTCATAGTCTCAGCTCTG
5′ 3′

P2:

GGAGGCCCCTAGCGCCTGCACTCTCCTACCCCGAGTGCTATTATTGGCGTTA
5′ 3′

-30 -10 +1
GGAGGCCCCTAGCGCCTGCACTCTCCTACCCCGAGTGCTAATTATTGGCGTTA
5′ 3′

CONSENSUS MOTIF :GCACTC 7N CCGAGTGCTAAT

PALINDROMIC CONSENSUS MOTIF :GCACTC 9N GAGTGC

FIG. 2

```
1/1                                     31/11
GTG ACG ACC GCC AGC TCC AAG GTT GCC ATC AAG CCG CTC GAC GAG CGC ATC GTG GTC CAG
val thr thr ala ser ser lys val ala ile lys pro leu glu asp arg ile val val gln
61/21                                   91/31
CCG CTC GAC GCC GAG CAG ACC ACG GCT TCG GGC CTG GTC ATC CCG GAC ACC GCG AAG GAG
pro leu asp ala glu gln thr thr ala ser gly leu val ile pro asp thr ala lys glu
121/41                                  151/51
AAG CCC CAG GAG GGC GTC GTC CTC GCG GTC GGC CCG GGC CGC TTC GAG AAC GGC GAG CGC
lys pro gln glu gly val val leu ala val gly pro gly arg phe glu asn gly glu arg
181/61                                  211/71
CTG CCG CTC GAC GTC AAG ACC GGC GAC CTC GTG CTG TAC AGC AAG TAC GGC GGC ACC GAG
leu pro leu asp val lys thr gly asp val val leu tyr ser lys tyr gly gly thr glu
241/81                                  271/91
GTC AAG TAC AAC GGC GAG GAG TAC CTC GTC CTC TCG GCC CGC GAC GTT CTC GCC ATC ATC
val lys tyr asn gly glu glu tyr leu val leu ser ala arg asp val leu ala ile ile
301/101
GAG AAG TAG
glu lys AMB
```

FIG. 5

```
1/1                                         31/11
ATG GCG AAG ATT CTG AAG TTC GAC GAG GAC GCC CGT CGC GCC CTT GAG CGC GGC GTG AAC
Met ala lys ile leu lys phe asp glu asp ala arg arg ala leu glu arg gly val asn
61/21                                       91/31
CAG CTG GCC GAC ACC GTC AAG GTG ACC ATC GGC CCC AAG GGC CGC AAC GTC GTC ATC GAC
gln leu ala asp thr val lys val thr ile gly pro lys gly arg asn val val ile asp
122/41                                      151/51
AAG AAG TTC GGC GCC CCG ACC ATC ACC AAC GAC GGC GTC ACC ATC GCC CGT GAG GTC GAG
lys lys phe gly ala pro thr ile thr asn asp gly val thr ile ala arg glu val glu
181/61                                      211/71
TGC GAC GAC CCG TAC GAG AAC CTC GGC GCC CAG CTC GTC AAG GAG GTG GCG ACC AAG ACC
cys asp asp pro tyr glu asn leu gly ala gln leu val lys glu val ala thr lys thr
241/81                                      271/91
AAC GAC ATC GCG GGT GAC GGC ACC ACC ACC GCG ACC GTG CTG GCC CAG GCG CTG GTC CGC
asn asp ile ala gly asp gly thr thr thr ala thr val leu ala gln ala leu val arg
301/101                                     331/111
GAG GGC CTG CGC AAC GTC GCC GCC GGC GCC TCC CCG GCC GCC CTG AAG AAG GGC ATC GAC
glu gly leu arg asn val ala ala gly ala ser pro ala ala leu lys lys gly ile asp
361/121                                     391/131
GCC GCC GTC GCC GCC GTC TCC GCC GAG CTG CTC GAC ACC GCG CGC CCG ATC GAC GAC AAG
ala ala val ala ala val ser ala glu leu leu asp thr ala arg pro ile asp asp lys
421/141                                     451/151
TCC GAC ATC GCC GCC GTC GCC GCG CTC TCC GCG CAG GAC AAG CAG GTC GGC GAG CTC ATC
ser asp ile ala ala val ala ala leu ser ala gln asp lys gln val gly glu leu ile
```

FIG. 6A

```
481/161                                                     511/171
GCC GAG GCG ATG GAC AAG GTC GGC AAG GAC GGT GTC ATC ACC GTC GAG GAG TCC AAC ACC
ala glu ala met asp lys val gly lys asp gly val ile thr val glu glu ser asn thr
541/181                                                     571/191
TTC GGT GTC GAC CTG GAC TTC ACC GAG GGC ATG GCC TTC GAC AAG GGC TAC CTG TCC CCG
phe gly val asp leu asp phe thr glu gly met ala phe asp lys gly tyr leu ser pro
601/201                                                     631/211
TAC ATG GTG ACC GAC CAG GAG CGT ATG GAG GCC GTC CTC GAC GAC CCG TAC ATC CTG ATC
tyr met val thr asp gln glu arg met glu ala val leu asp asp pro tyr ile leu ile
661/221                                                     691/231
CAC CAG GGC AAG ATC GGT TCG ATC CAG GAC CTG CTG CCG CTG CTG GAG AAG GTC ATC CAG
his gln gly lys ile gly ser ile gln asp leu leu pro leu leu glu lys val ile gln
721/241                                                     751/251
GCG GGT GGC TCC AAG CCG CTG CTG ATC ATC GCC GAG GAC GTC GAG GGC GAG GCC CTG TCG
ala gly gly ser lys pro leu leu ile ile ala glu asp val glu gly glu ala leu ser
781/261                                                     811/271
ACC CTG GTG GTC AAC AAG ATC CGC GGC ACG TTC AAC GCC GTC GCC GTC AAG GCG CCC GGC
thr leu val val asn lys ile arg gly thr phe asn ala val ala val lys ala pro gly
841/281                                                     871/291
TTC GGT GAC CGC CGC AAG GCG ATG CTC GGC GAC ATG GCC ACC CTC ACC GGT GCC ACC GTC
phe gly asp arg arg lys ala met leu gly asp met ala thr leu thr gly ala thr val
901/301                                                     931/311
ATC GCC GAG GAG GTC GGC CTC AAG CTC GAC CAG GCC GGT CTG GAC GTG CTG GGC ACC GCC
Ile ala glu glu val gly leu lys leu asp gln ala gly leu asp val leu gly thr ala
```

FIG. 6B

```
961/321                                         991/331
CGC CGC GTC ACC GTC ACC AAG GAC GAC ACG ACC ATC GTG GAC GGC GGC GGC AAC GCC GAG
arg arg val thr val thr lys asp asp thr thr ile val asp gly gly gly asn ala glu
1021/341                                        1051/351
GAC GTC CAG GGC CGC GTC GCC CAG ATC AAG GCC GAG ATC GAG TCG ACC GAC TCG GAC TGG
asp val gln gly arg val ala gln ile lys ala glu ile glu ser thr asp ser asp trp
1081/361                                        1111/371
GAC CGC GAG AAG CTC CAG GAG CGC CTC GCC AAG CTG GCC GGC GGC GTC TGC GTG ATC CGC
asp arg gln lys leu gln glu arg leu ala lys leu ala gly gly val cys val ile arg
1141/381                                        1171/391
GTC GGC GCG GCC ACC GAG GTC GAG CTG AAG GAG CGC AAG CAC CGT CTG GAG GAC GCC ATC
val gly ala ala thr glu val glu leu lys glu arg lys his arg leu glu asp ala ile
1201/401                                        1231/411
TCC GCG ACC CGC GCC GCG GTC GAG GAG GGC ATC GTC TCC GGT GGT GGC TCC GCG CTG GTC
ser ala thr arg ala ala val glu glu gly ile val ser gly gly gly ser ala leu val
1261/421                                        1291/431
CAC GCC GTC AAG GTC CTG GAC GAC AAC CTC GGC CGC ACC GGC GAC GAG GCC ACC GGT GTC
his ala val lys val leu asp asp asn leu gly arg thr gly asp glu ala thr gly val
```

FIG. 6C

```
         |    10     |    20     |    30     |    40     |    50     |    60
   1 CCGGCCGGGC TGAGGTTGGC TGGCTGGCCG GGTTCGGCCG GTGGGTCGAG GTGGCCTGGC 60
  61 CGGGCTCGCC AGGGTGAGTT GGCCGAGCCG AGGCGGCCCC GGGGCTCCCC GGGCCGAGTT 120
 121 GGCGCGGCCA GGCCAGGGCT CAGCAGGGTG GGGGAGTGGG GCAGGCGGCC CGGTAGGGGA 180
 181 GTGCGGGAGG GCAGCGCGCG CCGCGCGCAT TGGCACTCCG CTTGACCGAG TGCTAATCGC 240
 241 GGTCATAGTC TCAGCTCTGG CACTCCCCGC AGGAGAGTGC CAACACAGCG ACGGGCAGGT 300
 301 CCGGCACCCG CGACGACGGA TCGACCTGGT CGCCACACTC AGATCAGTTA ACCCCGTGAT 360
 361 CTCCGAAGGG GGAGGTCGGA TCGTGACGAC CGCCAGCTCC AAGGTTGCCA TCAAGCCGCT 420
 421 CGAGGACCGC ATCGTGGTCC AGCCGCTCGA CGCCGAGCAG ACCACGGCTT CGGGCCTGGT 480
 481 CATCCCGGAC ACCGCGAAGG AGAAGCCCCA GGAGGGCGTC GTCCTCGCGG TCGGCCCGGG 540
 541 CCGCTTCGAG AACGGCGAGC GCCTGCCGCT CGACGTCAAG ACCGGCGACG TCGTGCTGTA 600
 601 CAGCAAGTAC GGCGGCACCG AGGTCAAGTA CAACGGCGAG GAGTACCTCG TCCTCTCGGC 660
 661 CCGCGACGTT CTCGCCATCA TCGAGAAGTA GCAGGCCGGA GCGGTCCGGG CGCGAGCCCG 720
 721 GACGGCAGAC TCCACCTTTT TCCTGAAGCG CGCCCCTGGC CCCCGCGAGT GTTTGCCGGG 780
 781 TGGCGAGGGG CGCCTTTCAT TTCGAGAGCG CGGCGGCAGG CCGCTCCGAG AGGATTCGAA 840
 841 AAGCTCCCAT GGCGAAGATT CTGAAGTTCG ACGAGGACGC CCGTCGCGCC CTTGAGCGCG 900
 901 GCGTGAACCA GCTGGCCGAC ACCGTCAAGG TGACCATCGG CCCCAAGGGC CGCAACGTCG 960
 961 TCATCGACAA GAAGTTCGGC GCCCCGACCA TCACCAACGA CGGCGTCACC ATCGCCCGTG 1020
1021 AGGTCGAGTG CGACGACCCG TACGAGAACC TCGGCGCCCA GCTCGTCAAG GAGGTGGCGA 1080
```

FIG. 7A

```
1081 CCAAGACCAA CGACATCGCG GGTGACGGCA CCACCACCGC GACCGTGCTG GCCCAGGCGC 1140
1141 TGGTCCGCGA GGGCCTGCGC AACGTCGCCG CCGGCGCCTC CCCGGCCGCC CTGAAGAAGG 1200
1201 GCATCGACGC CGCCGTCGCC GCCGTCTCCG CCGAGCTGCT CGACACCGCG CGCCCGATCG 1260
1261 ACGACAAGTC CGACATCGCC GCCGTCGCCG CGCTCTCCGC GCAGGACAAG CAGGTCGGCG 1320
1321 AGCTCATCGC CGAGGCGATG GACAAGGTCG GCAAGGACGG TGTCATCACC GTCGAGGAGT 1380
1381 CCAACACCTT CGGTGTCGAC CTGGACTTCA CCGAGGGCAT GGCCTTCGAC AAGGGCTACC 1440
1441 TGTCCCCGTA CATGGTGACC GACCAGGAGC GTATGGAGGC CGTCCTCGAC GACCCGTACA 1500
1501 TCCTGATCCA CCAGGGCAAG ATCGGTTCGA TCCAGGACCT GCTGCCGCTG CTGGAGAAGG 1560
1561 TCATCCAGGC GGGTGGCTCC AAGCCGCTGC TGATCATCGC CGAGGACGTC GAGGGCGAGG 1620
1621 CCCTGTCGAC CCTGGTGGTC AACAAGATCC GCGGCACGTT CAACGCCGTC GCCGTCAAGG 1680
1681 CGCCCGGCTT CGGTGACCGC CGCAAGGCGA TGCTCGGCGA CATGGCCACC CTCACCGGTG 1740
1741 CCACCGTCAT CGCCGAGGAG GTCGGCCTCA AGCTCGACCA GGCCGGTCTG GACGTGCTGG 1800
1801 GCACCGCCCG CCGCGTCACC GTCACCAAGG ACGACACGAC CATCGTGGAC GGCGGCGGCA 1860
1861 ACGCCGAGGA CGTCCAGGGC CGCGTCGCCC AGATCAAGGC CGAGATCGAG TCGACCGACT 1920
1921 CGGACTGGGA CCGCGAGAAG CTCCAGGAGC GCCTCGCCAA GCTGGCCGGC GGCGTCTGCG 1980
1981 TGATCCGCGT CGGCGCGGCC ACCGAGGTCG AGCTGAAGGA GCGCAAGCAC CGTCTGGAGG 2040
2041 ACGCCATCTC CGCGACCCGC GCCGCGGTCG AGGAGGGCAT CGTCTCCGGT GGTGGCTCCG 2100
2101 CGCTGGTCCA CGCCGTCAAG GTCCTGGACG ACAACCTCGG CCGCACCGGC GACGAGGCCA 2160
2161 CCGGTGT                                                     2196

          | 10       | 20       | 30       | 40       | 50       | 60
```

FIG. 7B

```
1/1                                          31/11
ATG GCG AAG ATT CTG AAG TTC GAC GAG GAC GCC CGT CGC GCC CTT GAG CGC GGC GTG AAC
Met ala lys ile leu lys phe asp glu asp ala arg arg ala leu glu arg gly val asn
61/21                                        91/31
CAG CTG GCC GAC ACC GTC AAG GTG ACC ATC GGC CCC AAG GGC CGC AAC GTC GTC ATC GAC
gln leu ala asp thr val lys val thr ile gly pro lys gly arg asn val val ile asp
121/41                                       151/51
AAG AAG TTC GGC GCC CCG ACC ATC ACC AAC GAC GGC GTC ACC ATC GCC CGT GAG GTC GAG
lys lys phe gly ala pro thr ile thr asn asp gly val thr ile ala arg glu val glu
181/61                                       211/71
TGC GAC GAC CCG TAC GAG AAC CTC GGC GCC CAG CTC GTC AAG GAG GTG GCG ACC AAG ACC
cys asp asp pro tyr glu asn leu gly ala gln leu val lys glu val ala thr lys thr
241/81                                       271/91
AAC GAC ATC GCG GGT GAC GGC ACC ACC ACC GCG ACC GTG CTG GCG CAG GCG CTG GTC CGC
asn asp ile ala gly asp gly thr thr thr ala thr val leu ala gln ala leu val arg
301/101                                       331/111
GAG GGC CTG CGC AAC GTC GCC GCC GGC GCC TCC CCG GCC GCC CTG AAG AAG GGC ATC GAC
glu gly leu arg asn val ala ala gly ala ser pro ala ala leu lys lys gly ile asp
361/121                                       391/131
GCC GCC GTC GCC GCC GTC TCC GCC GAG CTG CTC GAC ACC GCG CGC CCG ATC GAC GAC AAG
ala ala val ala ala val ser ala glu leu leu asp thr ala arg pro ile asp asp lys
```

FIG. 8A

```
421/141                                 451/151
TCC GAC ATC GCC GCC GTC GCC GCG CTC TCC GCG CAG GAC AAG CAG GTC GGC GAG CTC ATC
ser asp ile ala ala val ala ala leu ser ala gln asp lys gln val gly glu leu ile
481/161                                 511/171
GCC GAG GCG ATG GAC AAG GTC GGC AAG GAC GGT GTC ATC ACC GTC GAG GAG TCC AAC ACC
ala glu ala met asp lys val gly lys asp gly val ile thr val glu glu ser asn thr
541/181                                 571/191
TTC GGT GTC GAC CTG GAC TTC ACC GAG GGC ATG GCC TTC GAC AAG GGC TAC CTG TCC CCG
phe gly val asp leu asp phe thr glu gly met ala phe asp lys gly tyr leu ser pro
601/201                                 631/211
TAC ATG GTG ACC GAC CAG GAG CGT ATG GAG GCC GTC CTC GAC GAC CCG TAC ATC CTG ATC
tyr met val thr asp gln glu arg met glu ala val leu asp asp pro tyr ile leu ile
661/221                                 691/231
CAC CAG GGC AAG ATC GGT TCG ATC CAG GAC CTG CTG CCG CTG CTG GAG AAG GTC ATC CAG
his gln gly lys ile gly ser ile gln asp leu leu pro leu leu glu lys val ile gln
721/241                                 751/251
GCG GGT GGC TCC AAG CCG CTG CTG ATC ATC GCC GAG GAC GTC GAG GGC GAG GCC CTG TCG
ala gly gly ser lys pro leu leu ile ile ala glu asp val glu gly glu ala leu ser
781/261                                 811/271
ACC CTG GTG GTC AAC AAG ATC CGC GGC ACG TTC AAC GCC GTC GCC GTC AAG GCG CCC GGC
thr leu val val asn lys ile arg gly thr phe asn ala val ala val lys ala pro gly
```

FIG. 8B

```
841/281                                 871/291
TTC GGT GAC CGC CGC AAG GCG ATG CTC GGC GAC ATG GCC ACC CTC ACC GGT GCC ACC GTC
phe gly asp arg arg lys ala met leu gly asp met ala thr leu thr gly ala thr val
901/301                                 931/311
ATC GCC GAG GAG GTC GGC CTC AAG CTC GAC CAG GCC GGT CTG GAC GTG CTG GGC ACC GCC
Ile ala glu glu val gly leu lys leu asp gln ala gly leu asp val leu gly thr ala
961/321                                 991/331
CGC CGC GTC ACC GTC ACC AAG GAC GAC ACG ACC ATC GTG GAC GGC GGC GGC AAC GCC GAG
arg arg val thr val thr lys asp asp thr thr ile val asp gly gly gly asn ala glu
1021/341                                1051/351
GAC GTC CAG GGC CGC GTC GCC CAG ATC AAG GCC GAG ATC GAG TCG ACC GAC TCG GAC TGG
asp val gln gly arg val ala gln ile lys ala glu ile glu ser thr asp ser asp trp
1081/361                                1111/371
GAC CGC GAG AAG CTC CAG GAG CGC CTC GCC AAG CTG GCC GGC GGC GTC TGC GTG ATC CGC
asp arg glu lys leu gln glu arg leu ala lys leu ala gly gly val cys val ile arg
1141/381                                1171/391
GTC GGC GCG GCC ACC GAG GTC GAG CTG AAG GAG CGC AAG CAC CGT CTG GAG GAC GCC ATC
val gly ala ala thr glu val glu leu lys glu arg lys his arg leu glu asp ala ile
1201/401                                1231/411
TCC GCG ACC CGC GCC GCG GTC GAG GAG GGC ATC GTC TCC GGT GGT GGC TCC GCG CTG GTC
ser ala thr arg ala ala val glu glu gly ile val ser gly gly gly ser ala leu val
```

FIG. 8C

```
1261/421                                1291/431
CAC GCC GTC AAG GTC CTG GAC GAC AAC CTC GGC CGC ACC GGC GAC GAG GCC ACC GGT GTC
his ala val lys val leu asp asp asn leu gly arg thr gly asp glu ala thr gly val
1321/441                                1351/451
GCG GTC GTC CGC CGC GCC GCC GTC GAG CCG CTG CGC TGG ATC GCC GAG AAC GCC GGC CTC
ala val val arg arg ala ala val glu pro leu arg trp ile ala glu asn ala gly leu
1381/461                                1411/471
GAG GGC TAC GTC ATC ACC ACC AAG GTG GCG GAG CTC GAC AAG GGC CAG GGC TTC AAC GCG
glu gly tyr val ile thr thr lys val ala glu leu asp lys gly gln gly phe asn ala
1441/481                                1471/491
GCC ACC GGC GAG TAC GGC CAC CTG GTC AAG GCC GGC GTC ATC GAC CCG GTC AAG GTC ACC
ala thr gly glu tyr gly asp leu val lys ala gly val ile asp pro val lys val thr
1501/501                                1531/511
CGC TCC GCC CTG GAG AAC GCG GCC TCC ATC GCC TCC CTG CTG CTG ACG ACC GAG ACC CTG
arg ser ala leu glu asn ala ala ser ile ala ser leu leu leu thr thr glu thr leu
1561/521                                1591/531
GTC GTC GAG AAG CCG GCC GAG GAG GAG CCC GAG GCC GGT CAC GGT CAC GGG CAC AGC CAC
val val glu lys pro ala glu glu glu pro glu ala gly his gly his gly his ser his
```

FIG. 8D

```
         |    10     |    20     |    30     |    40     |    50     |    60
   1 CCGGCCGGGC TGAGGTTGGC TGGCTGGCCG GGTTCGGCCG GTGGGTCGAG GTGGCCTGGC 60
  61 CGGGCTCGCC AGGGTGAGTT GGCCGAGCCG AGGCGGCCCC GGGGCTCCCC GGGCCGAGTT 120
 121 GGCGCGGCCA GGCCAGGGCT CAGCAGGGTG GGGGAGTGGG GCAGGCGGCC CGGTAGGGGA 180
 181 GTGCGGGAGG GCAGCGCGCG CCGCGCGCAT TGGCACTCCG CTTGACCGAG TGCTAATCGC 240
 241 GGTCATAGTC TCAGCTCTGG CACTCCCCGC AGGAGAGTGC CAACACAGCG ACGGGCAGGT 300
 301 CCGGCACCCG CGACGACGGA TCGACCTGGT CGCCACACTC AGATCAGTTA ACCCCGTGAT 360
 361 CTCCGAAGGG GGAGGTCGGA TCGTGACGAC CGCCAGCTCC AAGGTTGCCA TCAAGCCGCT 420
 421 CGAGGACCGC ATCGTGGTCC AGCCGCTCGA CGCCGAGCAG ACCACGGCTT CGGGCCTGGT 480
 481 CATCCCGGAC ACCGCGAAGG AGAAGCCCCA GGAGGGCGTC GTCCTCGCGG TCGGCCCGGG 540
 541 CCGCTTCGAG AACGGCGAGC GCCTGCCGCT CGACGTCAAG ACCGGCGACG TCGTGCTGTA 600
 601 CAGCAAGTAC GGCGGCACCG AGGTCAAGTA CAACGGCGAG GAGTACCTCG TCCTCTCGGC 660
 661 CCGCGACGTT CTCGCCATCA TCGAGAAGTA GCAGGCCGGA GCGGTCCGGG CGCGAGCCCG 720
 721 GACGGCAGAC TCCACCTTTT TCCTGAAGCG CGCCCCTGGC CCCCGCGAGT GTTTGCCGGG 780
 781 TGGCGAGGGG CGCCTTTCAT TTCGAGAGCG CGGCGGCAGG CCGCTCCGAG AGGATTCGAA 840
 841 AAGCTCCCAT GGCGAAGATT CTGAAGTTCG ACGAGGACGC CCGTCGCGCC CTTGAGCGCG 900
 901 GCGTGAACCA GCTGGCCGAC ACCGTCAAGG TGACCATCGG CCCCAAGGGC CGCAACGTCG 960
 961 TCATCGACAA GAAGTTCGGC GCCCCGACCA TCACCAACGA CGGCGTCACC ATCGCCCGTG 1020
1021 AGGTCGAGTG CGACGACCCG TACGAGAACC TCGGCGCCCA GCTCGTCAAG GAGGTGGCGA 1080
1081 CCAAGACCAA CGACATCGCG GGTGACGGCA CCACCACCGC GACCGTGCTG GCCCAGGCGC 1140
1141 TGGTCCGCGA GGGCCTGCGC AACGTCGCCG CCGGCGCCTC CCCGGCCGCC CTGAAGAAGG 1200
1201 GCATCGACGC CGCCGTCGCC GCCGTCTCCG CCGAGCTGCT CGACACCGCG CGCCCGATCG 1260
1261 ACGACAAGTC CGACATCGCC GCCGTCGCCG CGCTCTCCGC GCAGGACAAG CAGGTCGGCG 1320
```

FIG. 9A

```
1321 AGCTCATCGC CGAGGCGATG GACAAGGTCG GCAAGGACGG TGTCATCACC GTCGAGGAGT 1380
1381 CCAACACCTT CGGTGTCGAC CTGGACTTCA CCGAGGGCAT GGCCTTCGAC AAGGGCTACC 1440
1441 TGTCCCCGTA CATGGTGACC GACCAGGAGC GTATGGAGGC CGTCCTCGAC GACCCGTACA 1500
1501 TCCTGATCCA CCAGGGCAAG ATCGGTTCGA TCCAGGACCT GCTGCCGCTG CTGGAGAAGG 1560
1561 TCATCCAGGC GGGTGGCTCC AAGCCGCTGC TGATCATCGC CGAGGACGTC GAGGGCGAGG 1620
1621 CCCTGTCGAC CCTGGTGGTC AACAAGATCC GCGGCACGTT CAACGCCGTC GCCGTCAAGG 1680
1681 CGCCCGGCTT CGGTGACCGC CGCAAGGCGA TGCTCGGCGA CATGGCCACC CTCACCGGTG 1740
1741 CCACCGTCAT CGCCGAGGAG GTCGGCCTCA AGCTCGACCA GGCCGGTCTG GACGTGCTGG 1800
1801 GCACCGCCCG CCGCGTCACC GTCACCAAGG ACGACACGAC CATCGTGGAC GGCGGCGGCA 1860
1861 ACGCCGAGGA CGTCCAGGGC CGCGTCGCCC AGATCAAGGC CGAGATCGAG TCGACCGACT 1920
1921 CGGACTGGGA CCGCGAGAAG CTCCAGGAGC GCCTCGCCAA GCTGGCCGGC GGCGTCTGCG 1980
1981 TGATCCGCGT CGGCGCGGCC ACCGAGGTCG AGCTGAAGGA GCGCAAGCAC CGTCTGGAGG 2040
2041 ACGCCATCTC CGCGACCCGC GCCGCGGTCG AGGAGGGCAT CGTCTCCGGT GGTGGCTCCG 2100
2101 CGCTGGTCCA CGCCGTCAAG GTCCTGGACG ACAACCTCGG CCGCACCGGC GACGAGGCCA 2160
2161 CCGGTGTCGC GGTCGTCCGC CGCGCCGCCG TCGAGCCGCT GCGCTGGATC GCCGAGAACG 2220
2221 CCGGCCTCGA GGGCTACGTC ATCACCACCA AGGTGGCGGA GCTCGACAAG GGCCAGGGCT 2280
2281 TCAACGCGGC CACCGGCGAG TACGGCGACC TGGTCAAGGC CGGCGTCATC GACCCGGTCA 2340
2341 AGGTCACCCG CTCCGCCCTG GAGAACGCGG CCTCCATCGC CTCCCTGCTC CTGACGACCG 2400
2401 AGACCCTGGT CGTCGAGAAG CCGGCCGAGG AGGAGCCCGA GGCCGGTCAC GGTCACGGGC 2460
2461 ACAGCCACTG AGGCTGACCC CTTCCGCAGC CGAGGCCCGG CTCCCCGTCG CGGGGAGCCG 2520
2521 GGCCTCCGGC GTGTCCGGGA CCCCCCGGGA CGCGCGACGC CTACCGCGGC CCGTACTTGC 2580
2581 GGCCGGTACG CGAGGTCATC CCGGTCAGCA GGGCCCGCGG GGTCAGCTTC ACCAGGCCCA 2640
2641 TCAGCGCCTT GTACCGAGGG TCCGGGAT                                    2668
          |  10      |  20      |  30      |  40      |  50      |  60
```

FIG. 9B

REGULATORY NUCLEOTIDE SEQUENCE OF THE INITIATION OF TRANSCRIPTION

This application is a continuation of application Ser. No. 08/050,313, filed as PCT/FR91/00701 Sep. 3, 1991, published as WO92/04452, Mar. 19, 1992, abandoned.

BACKGROUND OF THE INVENTION (i) Field of the Invention

The invention relates to a regulatory nucleotide sequence of the initiation of transcription and its use in the production of polypeptides by the recombinant approach. The technical problem which presented itself when the present invention was being developed was to identify a strong and, if possible, thermoinducible promoter, which could be used in a large number of micro-organisms and, in particular, in the Actinomycetes.

(ii) Description of Related Art

The Actinomycetes constitute a bacterial order of great economic and medical importance, mention needs only to be made of the fact that the Actinomycetes include, in particular, the Streptomyces and Mycobacterium genera.

The Streptomyces are used for the production of about 70% of the antibiotics sold today; furthermore, even though there is no longer occasion to describe the ravages caused by *Mycobacterium tuberculosis* and *Mycobacterium leprae*, great interest is attached to the expression of the heterologous antigen in a strain of *M. bovis* BCG in order to produce a living polyvalent strain to be used as a vaccine.

The genetics of these bacteria has been little studied at the molecular level, but the regulation of genetic expression seems to be different from that which has been described for bacteria which have been studied in more detail such as *Escherichia coli* or *Bacillus subtilis.*

In particular, the Actinomycetes, the DNA of which is rich in G+C, recognize the "promoter" sequences in *Escherichia coli* and *Bacillus subtilis*, poorly or not at all. Baird et al. (J. Gen. Microbiol.1989, 135, 931–939) studied the genes coding for heat shock proteins in Mycobacterium and postulated that two sequences, TTGAG and TCTCATGT, located upstream from the sequence coding for the heat shock protein of 10 kDA of *Mycobacterium tuberculosis*, constitute the −35 and −10 regions of the promoter.

In fact, the two sequences exhibit a high degree of homolgy with the consensus sequence of the promoter in *E. coli*. Furthermore, sequences located upstream from the genes coding for other heat shock proteins in various species of Mycobacterium (for example, the protein of 65 kDa of *Mycobacterium leprae* or that of 64 kDA in *M. bovis*) also contain a couple of sequences of the same type, i.e.: TFGCCG and TTTCAT, or TTGCCG and CTTCAT, and which thus show a high degree of homology with the *E. coli* promoter and with the "−35 and −10" sequences of the 10 kDa species of *Mycobacterium tuberculosis.*

According to that article and the one by Thole et al. (Infection and Immunity, 55, 1987, 1466–1475), the promoters responsible for the transcription of the genes of the heat shock proteins in Mycobacterium contain, as −35 and −10 sequences, this type of coupled sequences. These sequences will be designated subsequently as "−10 and −35 sequences of the *E. coli* type". This being so, the authors had not confirmed this hypothesis by mapping and the identity of the promoters consequently remains uncertain.

In a surprising manner, the present inventors have noticed that the −10 and −35 sequences of the *E. coli* type are also present in Streptomyces, but do not play a role in the initiation of the transcription of heat shock proteins in the bacteria of this genus. It should be noted that, in the articles mentioned above, Baird and Thole had also observed the presence, in sequences upstream from the genes coding for the heat shock proteins in Mycobacterium, a palindromic motif containing the sequence (SEQ ID NO:1) GCACTC 9N GAGTGC. However, the precise role of this motif had not been identified. Thole postulates that this motif is implicated either in the termination of transcription of an operon located upstream from the gene coding for the heat shock protein or in the regulation of the translation of a polycistronic messenger.

With the aim of cloning a strong (and, if possible, thermoinducible) promoter, which can be used in a large number of Actinomycetes, the inventors have studied the response to heat shock in Streptomyces and have cloned a strongly expressed protein in order to characterize its promoter. In fact, the response phenomenon to heat shock resulting in the de novo of proteins is a universal phenomenon; it may thus be anticipated that its regulation will be similar in various Actinomycetes and in particular that the promoters will have consensus sequences which will enable them to be used in a large number of strains.

SUMMARY OF THE INVENTION

The inventors have thus identified and characterized two functional promoters in the Streptomyces and, in addition, have been able to identify the function of the said palindrome as a consequence of the observation that each of these promoters contains the motif (SEQ ID NO:1) GCACTC 9N GAGTGC.

The invention relates to a recombinant nucleotide sequence characterized in that it comprises:

- a regulatory sequence of the initiation of transcription, this regulatory sequence containing a promoter in combination with the motif (SEQ ID NO:1) GCACTC 9N GAGTGC in which "N" signifies any one of the 4 bases : thymine, guanine, adenine and cytosine;
- a sequence coding for a polypeptide, called "heterologous polypeptide", other than that naturally associated with the said promoter;

the said coding sequence being positioned downstream from the said regulatory sequence of the initiation of transcription at a site which, under suitable conditions, would permit the polypeptide under the control of the said promoter to be expressed.

The recombinant nucleotide sequence of the invention is capable of giving rise to the expression of a heterologous gene in a cell containing it.

The regulatory sequence of the initiation of transcription, which forms part of the recombinant nucleotide sequence, is composed of a promoter in association with the motif (SEQ ID NO:1) GCACTC 9N GAGTGC. In this context, "in association" means that the motif (SEQ ID NO:1) GCACTC 9N GAGTGC may be distinct from the promoter or it may be contained, at least in part, within the promoter. This latter possibility includes the situation in which the motif overlaps the promoter sequence and the situation in which the motif constitutes an integral part of the promoter.

Promoters associated with the sequence (SEQ ID NO:1) GCACTC 9N GAGTGC which are particularly preferred according to the invention are the promoters present in the Actinomycetes and, more particularly, those which in the bacterial genome are normally associated with heat shock proteins. As examples of this type of promoter, mention may be made of the promoters of heat shock proteins of 18 kDA (P1) and 56 kDa (P2) in *Streptomyces albus* identified within the framework of the invention by the inventors:

P1 corresponding to one of the sequences (SEQ ID NOS. 2–3):

CATTGGCACTCCGCTTGACCGAGTGCTAATCGCGGTCATAGTCTCAGCTCTG
5' 3' or

GCATTGGCACTCCGCTTGACCGAGTGCTAATCGCGGTCATAGTCTCAGCTCTG
5' 3'

P2 corresponding to one of the sequences (SEQ ID NOS. 4–5):

GGAGGCCCCTAGCGCCTGCACTCTCCTACCCCGAGTGCTATTATTGGCGTTA
5' 3' or

GGAGGCCCCTAGCGCCTGCACTCTCCTACCCCGAGTGCTAATTATTGGCGTTA
5' 3'

Each of these promoters may be shortened by a maximum of 4 or 5 bases at the 5' end without adversely affecting its activity. Other types of promoters are those for heat shock proteins of 10 kDa and 65 kDa from *Mycobacterium tuberculosis*, 64 kDa from *M. bovis* and 65 kDa from *M. leprae*.

The association of the GCACTC 9N GAGTGC motif with the promoter confers thermoinducible character on the promoter. It is probable that this sequence is an operator and constitutes the binding site for a repressor, which thus prevents the RNA polymerase from binding to the −10 and −35 sequences of the promoter. In the case in which the motif is distinct from the promoter, it is preferably upstream from the promoter, by about 150 to 200 bases, for example.

The recombinant sequence of the invention contains, in addition, to the regulatory sequence of the initiation of transcription, a sequence coding for a polypeptide called "heterologous polypeptide", different from that which is naturally associated with the said promoter. Thus, the immediate genetic environment of the promoter is different from that in the genome from which it is derived. As examples of types of heterologous polypeptides, mention may be made of neutralizing antigens which can be used in the production of recombinant live vaccines or polypeptides conferring resistance to an antibiotic, enzymes, etc. . . .

In the nucleotide sequence of the invention, the coding sequence is positioned downstream from the said regulatory sequence. Their relative positions are, of course, such that the expression of the coding sequence takes place under the control of the promoter.

In addition, the invention relates to an expression vactor containing the nucleotide sequence of the invention, for example a plasmid.

The invention also relates to a cell transformed by this expression vector, the said cell being capable of recognizing the promoter used in the regulatory sequence of the initiation of transcription. The transformed cells are preferably prokaryotic cells and, more particularly, prokaryotes belonging to the order of the Actinomycetes, for example Streptomyces or Mycobacterium.

The invention also relates to a procedure for the production of a polypeptide characterized in that it comprises the following steps:

transformation of a cell by an expression vector according to the invention under conditions allowing the expression of the said polypeptide, the said cell being capable of recognizing the said promoter;

recovery of the polypeptide expressed.

The conditions allowing the expression of the polypeptide are those known from the prior art and in the present case, preferably include the use of heat shock, which has the effect of inducing expression. The heat shock may be an increase in temperature from about 37° C. to 45° C. or, in particular, 40° C. to 45° C., for example 37° C. or 41° C. in Streptomyces, 42° C. to 45° C. in the case of Mycobacterium.

It is interesting to note that the use of the promoters P1 and P2 of the invention results in a sustained expression of the heterologous protein at high temperature, for example between 37° and 41° C. in Streptomyces.

Another feature of the invention relates to the possibility of transforming a promoter into a thermoinducible promoter as a result of its association with the (SEQ ID NO.1) GCACTC 9N GAGTGC motif. More particularly, this feature of the invention relates to a procedure for conferring a thermoinducible character on a promoter, characterized by the juxtaposition of a sequence containing the (SEQ ID NO.1) GCACTC 9N GAGTGC motif, on the one hand, and the promoter, on the other, the sequence containing the (SEQ ID NO.1) GCACTC 9N GAGTGC motif being positioned upstream from the promoter, or by insertion of the sequence containing the (SEQ ID NO.1) GCACTC 9N GAGTGC motif at a site which is, at least in part, contained within the promoter, this latter site being selected such that the simple insertion of the said palindrome does not perturb the activity of the promoter. The precise position in which the (SEQ ID NO.1) GCACTC 9N GAGTGC motif must be placed with respect to the promoter in order to be able to confer thermoinducible character may vary depending on the promoter used. This can be checked by detecting, on application of a heat shock, the expression of an easily detectable heterologous gene, for example a gene marker such as LacZ, in a cell transformed by the construction under test. The positioning of the (SEQ ID NO.1) GCACTC 9N GAGTGC motif at a site about 150 to 200 bases upstream from the promoter can confer this thermoinducible character. In some cases, the (SEQ ID NO.1) GCACTC 9N GAGTGC motif may be inserted at a site which is, at least in part, contained within the promoter. In such a case, the insertion site must be selected such that the simple insertion of the motif does not perturb the activity of the promoter other than that due to the introduction of the thermoinducible effect. It is important not to modify the −10 and −35 sequences of the promoter when this insertion is made. The thermoinducible character of the regulatory sequence of the initiation of transcription thus produced may be checked by applying the method described above. While they were studying the promoters, the inventors studied the response to heat shock of various species of Streptomyces. In addition to the principal heat shock proteins with molecular weights of 90–100, 70 and 56–58 kDa, a protein of 16 to 18 kDa was observed in each of the species tested. This protein (called HSP18) is produced at very high levels in *Streptomyces albus* when the culture is transferred from 30° to 37° C. and may constitute up to 10% of the total proteins. The induction by means of beat shock of the proteins of 70 and 90–100 kDa is transient, whereas that of the proteins of 56–58 kDa and 18 kDa is constitutive, the production being sustained at high temperatures.

The protein called HSP18 was purified and characterized. Its properties are unlike those of other heat shock proteins. For example, apart from its relatively small size and its being regulated constitutively at high temperature, it possesses an isoelectric point higher than 9. This very high isoelectric point is, however, not reflected in its amino acid composition (see Table 2).

Furthermore, the determination of its amino acid composition revealed a rather low methionine content, which is not consistent with the results of /35S/ methionine incorporation experiments (see Table 1). These observations suggest that the HSP18 protein undergoes modification which takes place after translation. The HSP18 protein does not react with polyclonal antibodies against the GroEL protein from *E. coli*, nor with monoclonal antibodies specific for the 65 kDa heat shock protein from *Mycobacterium leprae.*

A study of the transcription of the "groEL-1" gene coding for the HSP18 protein showed that HSP18 is, in fact, a truncated protein. The groEL-1 gene codes in reality for a protein of 56 kDa which is modified after translation and gives rise to the 18 kDa protein.

FIG. 6 shows the partial sequence of the groEL-1 gene and its amino acid translation product. This sequence corroborates the sequences determined by Edman degradation of HSP18. The sequence shown in FIG. 6 lacks the COOH terminus of the 56 kDa protein. The sequence of the 18 kDa protein is included in this parent sequence, their two NH2 termini being identical (amino acid No.1). HSP18 extends maximally up to about amino acid 170.

FIG. 8 gives the complete sequence of the protein encoded by the groEL-1 gene, which comprises the HSP18 protein, just like the figure shown in FIG. 6. The invention relates to a heat shock protein comprising either (i) the amino acid sequence shown in FIG. 6 or the sequence corresponding to the amino acid sequence shown in FIG. 8, or (ii) a sequence exhibiting at least 85% homology with this sequence, or (iii) a part of the sequence (i) or (ii) comprising the NH2 terminus and extending up to about amino acid 170, the polypeptide (iii) having a molecular weight of about 18 kDa and a very basic isoelectric point of about 9.

By analogy with the function of other proteins of the GroEL type, it is probable that HSP18 is essential for the survival of the cell and plays a role of "molecular chaperon", i.e. binds transiently to nascent polypeptides preventing the aggregation of insoluble proteins and making folding and transport through the cell membrane possible. It is also possible that HSP18 is implicated in the resistance of the strain to its own antibiotics or in tolerance to heat.

In accordance with a special feature, the invention also relates to a polypeptide containing the COOH terminal region of the GroEL-1 protein as shown in FIG. 8. A particular polypeptide corresponding to this definition contains or corresponds to the following amino acid sequence: Gly His Gly His Gly His Ser His.

The amino acid sequence described above corresponds to an original sequence of amino acids when compared with the COOH terminal peptide sequences known for heat shock proteins. This COOH terminal sequence might be implicated in the formation of the truncated 18 kDa protein.

BRIEF DESCRIPTION OF THE DRAWINGS

Various features of the invention are illustrated in the figures:

FIG. 2 (SEQ ID NOS. 1–6) shows the P2 promoter of groEL-2 and the P1 promoter of groES and groEL-1.

FIG. 5 (SEQ ID NO.7) shows the nucleotide sequence and the amino acid sequence deduced from the groES structural gene and the GroES protein.

FIGS. 6A–C (SEQ ID NO.8) illustrate the nucleotide sequence as well as the deduced amino acid sequence of the protein precursor of HSP18.

FIGS. 7A–B (SEQ ID NO.9) show the nucleotide sequence of the gro es el operon together with its promoter sequence.

FIGS. 8A–D (SEQ ID NO.10) show the complete amino acid sequence encoded by the groEL-1 gene with which it is aligned.

FIG. 9A–B (SEQ ID NO.11) shows the nucleotide sequence of the complete groEL-1 gene.

DETAILED DESCRIPTION OF PREFERRED EMBODIMENTS

EXAMPLES

Figure 1:
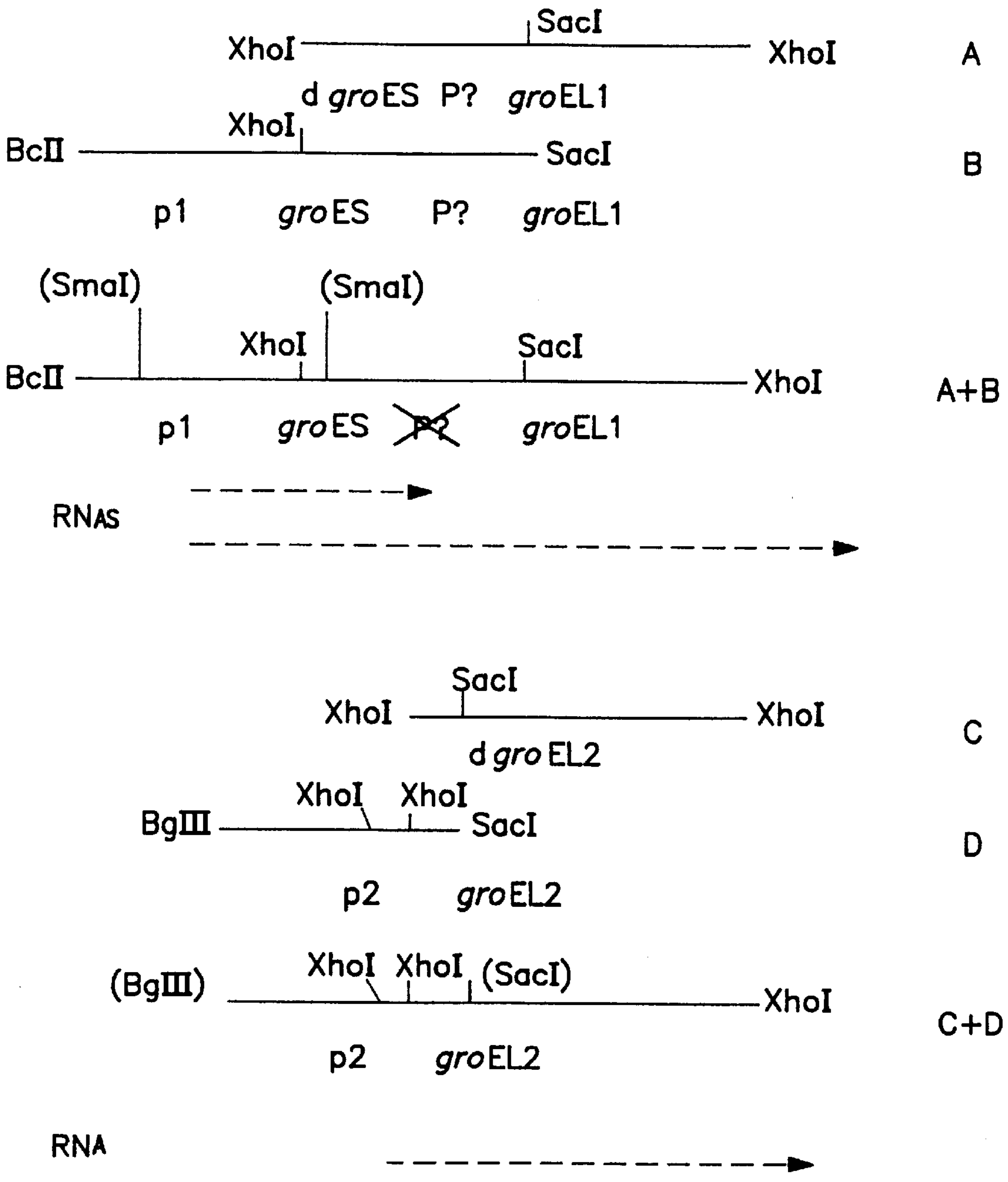
FIG. 1 shows schematically the cloning of the groEL-1, groES and groEL-2 genes. The sites which have served for the construction of the plasmids pPM1005 and pPM997+ Neo are shown in brackets.

Effect of Temperature on Protein Synthesis in Streptomyces:

The total protein extracts of 15 different species of Streptomyces were prepared before and after application of a heat shock (increase in temperature from 30° C. to 41° C.). Major heat shock proteins of 90–100, 70 and 56–58 kDa were detected on a SDS-PAGE gel, stained with Coomassie blue. In addition, a molecular band corresponding to a protein of 18 kDa was also observed in some species. This protein was very strongly induced in *Streptomyces albus.*

Immunological Properties of the Proteins:

A "Western blot" analysis of the proteins on the gel with monoclonal antibodies against the 65 kDa heat shock protein of *Mycobacterium leprae* and with polyclonal antibodies against the GroEL protein of *E. coli* was carried out. None of the proteins reacted with the monoclonal antibodies and only the 56–58 kDa HSPs reacted with the polyclonal antibodies.

Study of the Heat Shock Proteins in *Streptomyces albus:*

The response to heat shock in *Streptomyces albus* was analysed by means of electrophoresis of the total proteins at 30° C. and 41° C. The proteins were labelled for 40 minutes. The amino acids used were /35S/ methionine and /14C/ alainine. It was possible to visualise four major heat shock proteins. HSP90, which could not be detected at 30° C., represented about 3% of the total proteins after heat shock. The amount of HSP70 was at least doubled. HSP56–58 showed an increase of 30% and HSP18, which could not be detected before heat shock, represented 4 to 7% of the total proteins after the shock (see Table 1).

TABLE 1

QUANTIFICATION OF THE LEVELS OF SYNTHESIS OF THE MAJOR HEAT SHOCK PROTEINS AFTER LABELLING WITH 14C ALANINE AND 35S METHIONINE

| | Level of synthesis (a) at 30° C. and 41° C. | | | |
|---|---|---|---|---|
| Protein MW(b) | 35S/30° C. | 35S/41° C. | 14C/30° C. | 14C/41° C. |
| 90 | c | 3 | — | 2.9 |
| 70 | 2.7 | 6.4 | 2.3 | 5.8 |
| 56–58 | 6.8 | 8.4 | 6.2 | 9.0 |
| 18 | >0.7? | 6.9 | >0.7? | 3.8 |

a. expressed as a percentage of the total optical density (O.D.) measured by means of autoradiography.
b. apparent molecular weight in kDA.
c. not detected.

Study of the HSP18 of *Streptomyces albus:*

The 18 kDa protein of *Streptomyces albus* (HSP18), which is extremely basic, was purified and its partial amnino acid composition was determined (see Table 2):

TABLE 2

AMINO ACID COMPOSITION OF HSP18

| | |
|---|---|
| Asx | 12.2 |
| Thr | 9.4 |
| Ser | 3.2 |
| Gix | 10.8 |
| Ala | 12.1 |
| Cys | 0.0 |
| Met | 0.0 |
| Val | 9.2 |
| Ile | 5.7 |
| Leu | 6.8 |
| Tyr | 1.3 |
| Phe | 1.9 |
| His | 0.3 |
| Lys | 6.9 |
| Arg | 4.5 |
| Gly | 11.0 |
| Pro | 4.4 |

The sequence of the NH2 terminus and of two internal fragments of the protein were determined by means of Edman degradation.

Synthesis of Oligonucleotides:

Two degenerate nucleotide probes of 30 bases were synthesized on the basis of the peptide sequence of one of the internal fragments described above. The sequence of this fragment (SEQ ID NO.12) is:

. . . D-D-P-Y-E-N-L-G-A-Q. . . .

The following (SEQ ID NOS. 13–14) deoxyoligonucleotide probes were synthesized:

```
5' GAC—GAC—CCC—TAC—GAG—AAC—CTG—GGC—GCC—CA     3'OL1
              G                      C       T
3' CTG—CTG—GGG—ATG—CTC—TTG—GAC—CCG—CGG—GTC    5'OL2
              C                      G       A
```

Cloning of the Gene for the Thermoinducible Protein HSP18:

After hydridization at 60° C. in 5× SSC, these oligonucleotide probes have made it possible to characterize and clone a 1.9 kb XhoI restriction fragment of *Streptomyces albus* (see cloning A in FIG. 1).

This fragment was sequenced; it contains an open reading frame which extends from an ATG at position 430 to beyond the cloned region thus coding for a protein of more than 50 kDa, but the NH2 terminus of which corresponds to the nucleotide sequence deduced from the peptide sequence of HSP18. The amino acid sequence corresponding to this gene shows, in addition, a strong homology throughout its length with the heat-shock protein groEL of *E. coli* and the 65 kDa protein from *Mycobacterium leprae* (75% homology). Initially, this gene was called "groEL-1".

Demonstration and Cloning of a Second "groEL-like" Gene in *Streptomyces albus:*

Hybridizations of the genome of *Streptomyces albus* were carried out using the 5' part of the gene for HSP65 of *Mycobacterium leprae* as probe; this probe gives two signals after hybridization with the genome of *Streptomyces albus*, one strong and one weak, irrespective of the enzyme used to digest the DNA. The weak signal corresponds to the signals obtained with the oligonucleotides deduced from HSP18, i.e. to the groEL-1 gene. The strong signal corresponds to a gene coding for another "GroEL-like" protein of accepted size (65 kDa). There are thus two groEL-like genes in *Streptomyces albus.*

Cloning of the Gene for the Heat-Shock Protein HSP65 of *Streptomyces albus:*

The 1.2 kb XhoI restriction fragment strongly bound by the HSP65 probe from *Mycobacterium leprae* was cloned (cloning C in FIG. 1).

The nucleotide sequence of this fragment was determined. The 1.2 kb XhoI fragment codes for an internal fragment of a protein showing 90% homology with the 65 kDa protein from *Mycobacterium leprae*, in addition the two "groEL-like" genes 1 and 2 in *Streptomyces albus* show an 80% homology.

The gene coding for this 65 kDa protein was called groEL-2.

Study of the Transcription of the "groEL-like" Genes and the Search for the Promoters:

The total RNAs of the *Streptomyces albus* strain were extracted at various times during a heat shock experiment and treated according to the "Northern blot" technique, then hybridized with various oligonucleotides, the synthesis of which was based on either the groEL-1 sequence or the groEL-2 sequence and which were specific for each of the regions selected in these two sequences. The same nitrocellulose filters were used in repeat hybridizations with the totality of the two cloned fragments. Three very strongly thermoinducible transcripts are observed; their sizes are about 2500, 2100 and 650 bases, respectively. The one with 2100 bases corresponds to the groEL-2 transcript, the one with 650 bases to the transcript of the gene situated upstream from groEL-1; the one with 2500 bases to the co-transcription of groEL-1 and the gene situated upstream from groEL-1. These results showed, on the one hand, that the two genes groEL-1 and groEL-2 had indeed strong and inducible promoters, in particular thermoinducible promoters, and, on the other, that the groEL-1 promoter had not been cloned in the 1.9 kb fragment. In particular, these results show that none of the RNAs starts at the loop marked P? in FIG. 1, the sequence postulated as being capable of serving as promoter in Mycobacterium.

In fact, this loop contains two sequences, TTTGCCGGG and TTTCAT, which, in the absence of mapping data for thepromoter, were considered to be the −35 and −10 regions, respectively, of the promoter for the 65 kDa protein from Mycobacterium (see, for example, J. Gen. Microbiol. (1989), 135, 931–939). These results show that these two sequences do not form part of the promoter of the groEL-1 gene in *Streptomyces albus.*

The desired promoter would be expected to be situated upstream from the gene forming an operon with groEL-1. The gene situated upstream from groEL-1 has been identified; it is a gene showing strong homology to the groES gene of *E. coli* where it also forms an operon with groEL-1 (see FIG. 5).

Cloning of the Promoter Regions of the Two Genes groEL-1 and groEL-2:

Two novel fragments of *Streptomyces albus* DNA, hydrolysed by BclI/SacI (1700 bp) and BglII/SAcI (900 bp), were cloned with the aid of oligonucleotides synthesized starting from the sequence of the previously cloned fragments and described above. Hence they partially span the fragment bearing groEL-1 and that bearing groEL-2, respectively and extend upstream for about 800 bp in each case (clonings B and D in FIG. 1).

These fragments were sequenced, then the promoters were characterized by means of mapping using the S1 nuclease and by primer extension using the reverse transcriptase. The sequences of the promoters of the two genes groEL-1 and groEL-2 thus characterized are not identical (FIG. 2), but they show considerable structural homology, in particular both possess the following palindromic sequence:

GCACTC 9N GAGTGC

The sequences of the two promoters are the following:

P1 corresponding to one of the sequences (SEQ ID NOS. 2–3):

CATTGGCACTCCGCTTGACCGAGTGCTAATCGCGGTCATAGTCTCAGCTCTG
5' 3' or

GCATTGGCACTCCGCTTGACCGAGTGCTAATCGCGGTCATAGTCTCAGCTCTG
5' 3'

P2corresponding to one of the sequences (SEQ ID NOS. 4–5):

GGAGGCCCCTAGCGCCTGCACTCTCCTACCCCGAGTGCTATTATTGGCGTTA
5' 3' or

GGAGGCCCCTAGCGCCTGCACTCTCCTACCCCGAGTGCTAATTATTGGCGTTA
5' 3'

Figure 3:
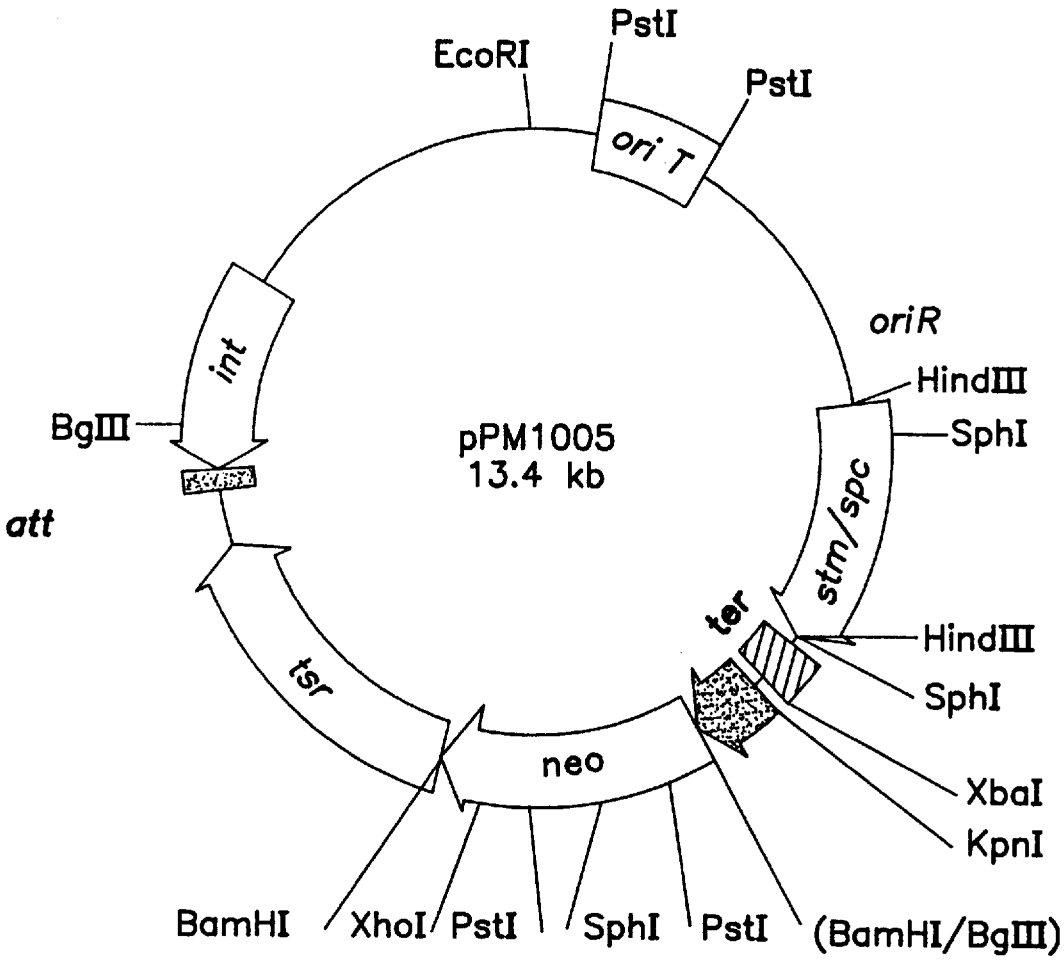
FIG. 3 shows the vector pPM1005 containing the neo gene of TN5 under the control of the SmaI fragment of 440 bp of *Streptomyces albus*. This fragment contains the P1 promoter and the first 160 base pairs of the groES gene.
Figure 4:
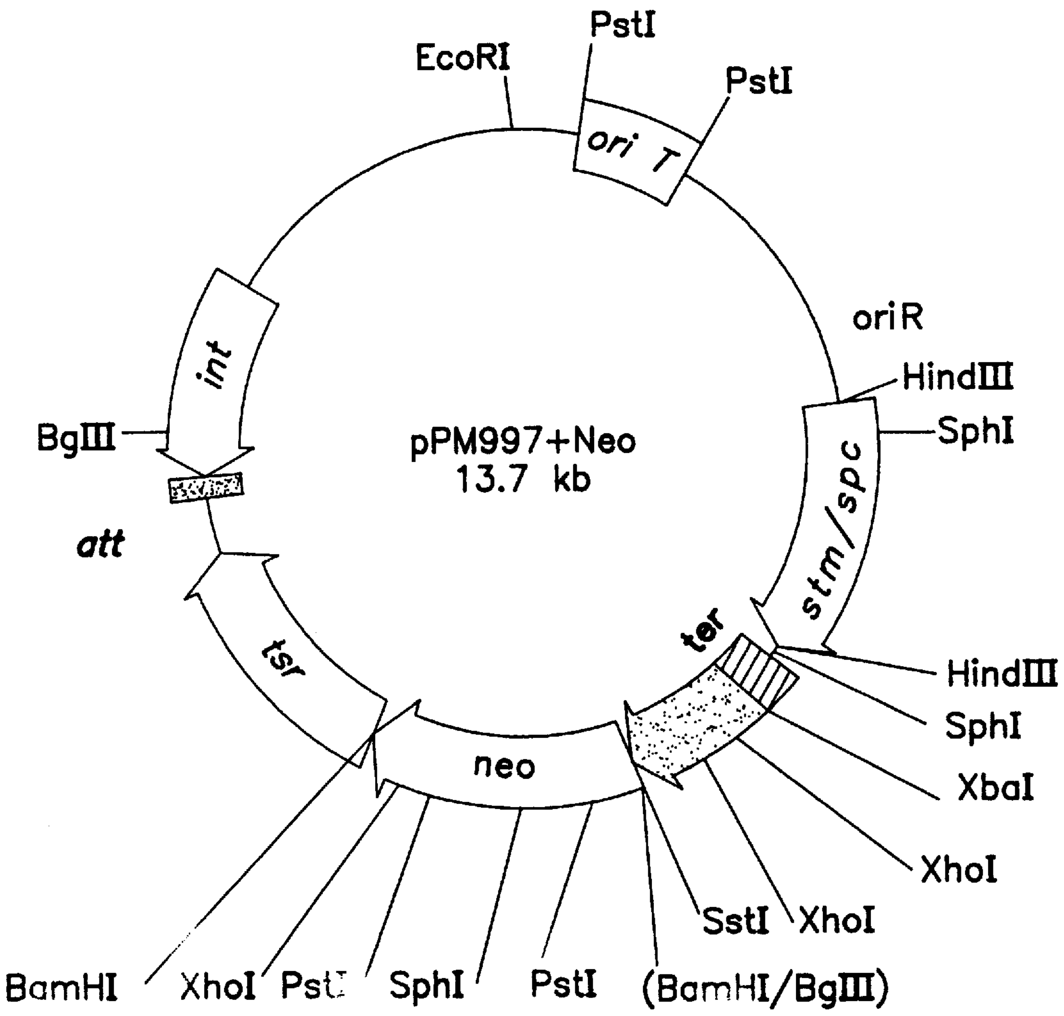
FIG. 4 shows the vector pPM997+Neo containing the neo gene of Tn5 under the control of the BglII/SstI fragment of 800 bp of *Streptomyces albus*. This fragment contains the P2 promoter and the first 183 bp of the groEL-2 gene.

Use of the Promoters of groEL-1 and groEL-2 for the Expression of a Heterologous Gene:

These two promoters were used for the expression of the heterologous neo gene of the transposon Tn5 of Klebsiella. This gene codes for an aminoglycoside phospho-transferase (APH) which confers resistance to neomycin/kanamycin. This gene was cloned downstream from the two promoters (FIGS. 3 and 4), then introduced into *Streptomyces albus* and also into *S. lividans*. The neo gene is then strongly expressed, as is shown by the considerable degree of resistance to these antibiotics which it confers; furthermore, we have been able to visualize the synthesis of the APH in crude extracts after electrophoresis on polyacrylamide gel and immuno-blotting with anti-APH antibodies. It must be emphasized that these results were obtained in Streptomyces with an integrating vector. Hence, in these experiments, there is only one copy of the neo gene and of the promoter under study per genome. In fact, in order to judge the strength of the promoter, it was important not to increase the expression of neo artificially by increasing the number of copies of it by using a vector which generates a large number of copies.

The HindIII-BamHI fragments of pPM1005 and the SmaI-SmaI fragments of pPM997 have also been inserted into Mycobacterium. The SmaI-SmaI fragment of pPM997 contains the neo gene, the P2 promoter and the terminator.

We claim:

1. A recombinant nucleotide sequence comprising:

a regulatory sequence for initiation of transcription, this regulatory sequence including a promoter contained in the SmaI-SmaI fragment of pPM1005 or in the BglII-SstI fragment of pPM997, operably linked to;

a sequence coding for a heterologous polypeptide different from that naturally associated with said promoter, wherein said coding sequence is positioned downstream from said regulatory sequence for initiation of transcription at a site which, under suitable conditions, allows the polypeptide to be expressed under the control of said promoter.

2. The recombinant nucleotide sequence according to claim 1, wherein the promoter comprises a GCACTC 9N GAGTGC (SEQ ID NO: 1) sequence.

3. An expression vector including a recombinant nucleotide sequence according to claim 1 which expresses the polypeptide.

4. An expression vector according to claim 3 which is a plasmid.

5. A heat shock polypeptide comprising:

either (i) one of the amino acid sequences (SEQ ID NOs:8 and 10) shown below;

or (ii) a part of this sequence (i), said part comprising the $NH_2$ terminus and said polypeptide having a molecular weight of about 18 kDa and an isoelectric point of about 9:

SEQ ID NO: 8:

```
1/1                                     31/11
ATG GCG AAG ATT CTG AAG TTC GAC GAG GAC GCC CGT CGC GCC CTT GAG CGC GGC GTG AAC
Met ala lys ile leu lys phe asp glu asp ala arg arg ala leu glu arg gly val asn

61/21                                   91/31
CAG CTG GCC GAC ACC GTC AAG GTG ACC ATC GGC CCC AAG GGC CGC AAC GTC GTC ATC GAC
gln leu ala asp thr val lys val thr ile gly pro lys gly arg asn val val ile asp

121/41                                  151/51
AAG AAG TTC GGC GCC CCG ACC ATC ACC AAC GAC GGC GTC ACC ATC GCC CGT GAG GTC GAG
lys lys phe gly ala pro thr ile thr asn asp gly val thr ile ala arg glu val glu

181/61                                  211/71
TGC GAC GAC CCG TAC GAG AAC CTC GGC GCC CAG CTC GTC AAG GAG GTG GCG ACC AAG ACC
cys asp asp pro tyr glu asn leu gly ala gln leu val lys glu val ala thr lys thr

241/81                                  271/91
AAC GAC ATC GCG GGT GAC GGC ACC ACC ACC GCG ACC GTG CTG GCC CAG GCG CTG GTC CGC
asn asp ile ala gly asp gly thr thr thr ala thr val leu ala gln ala leu val arg

301/101                                 331/111
GAG GGC CTG CGC AAC GTC GCC GCC GGC GCC TCC CCG GCC GCC CTG AAG AAG GGC ATC GAC
glu gly leu arg asn val ala ala gly ala ser pro ala ala leu lys lys gly ile asp

361/121                                 391/131
GCC GCC GTC GCC GCC GTC TCC GCC GAG CTG CTC GAC ACC GCG CGC CCG ATC GAC GAC AAG
ala ala val ala ala val ser ala glu leu leu asp thr ala arg pro ile asp asp lys

421/141                                 451/151
TCC GAC ATC GCC GCC GTC GCC GCG CTC TCC GCG CAG GAC AAG CAG GTC GGC GAG CTC ATC
ser asp ile ala ala val ala ala leu ser ala gln asp lys gln val gly glu leu ile

481/161                                 511/171
GCC GAG GCG ATG GAC AAG GTC GGC AAG GAC GGT GTC ATC ACC GTC GAG GAG TCC AAC ACC
ala glu ala met asp lys val gly lys asp gly val ile thr val glu glu ser asn thr

541/181                                 571/191
TTC GGT GTC GAC CTG GAC TTC ACC GAG GGC ATG GCC TTC GAC AAG GGC TAC CTG TCC CCG
phe gly val asp leu asp phe thr glu gly met ala phe asp lys gly tyr leu ser pro

601/201                                 631/211
TAC ATG GTG ACC GAC CAG GAG CGT ATG GAG GCC GTC CTC GAC GAC CCG TAC ATC CTG ATC
tyr met val thr asp gln glu arg met glu ala val leu asp asp pro tyr ile leu ile

661/221                                 691/231
CAC CAG GGC AAG ATC GGT TCG ATC CAG GAC CTG CTG CCG CTG CTG GAG AAG GTC ATC CAG
his gln gly lys ile gly ser ile gln asp leu leu pro leu leu glu lys val ile gln

721/241                                 751/251
GCG GGT GGC TCC AAG CCG CTG CTG ATC ATC GCC GAG GAC GTC GAG GGC GAG GCC CTG TCG
ala gly gly ser lys pro leu leu ile ile ala glu asp val glu gly glu ala leu ser

781/261                                 811/271
ACC CTG GTG GTC AAC AAG ATC CGC GGC ACG TTC AAC GCC GTC GCC GTC AAG GCG CCC GGC
thr leu val val asn lys ile arg gly thr phe asn ala val ala val lys ala pro gly

841/281                                 871/291
TTC GGT GAC CGC CGC AAG GCG ATG CTC GGC GAC ATG GCC ACC CTC ACC GGT GCC ACC GTC
phe gly asp arg arg lys ala met leu gly asp met ala thr leu thr gly ala thr val

901/301                                 931/311
ATC GCC GAG GAG GTC GGC CTC AAG CTC GAC CAG GCC GGT CTG GAC GTG CTG GGC ACC GCC
ile ala glu glu val gly leu lys leu asp gln ala gly leu asp val leu gly thr ala

961/321                                 991/331
CGC CGC GTC ACC GTC ACC AAG GAC GAC ACG ACC ATC GTG GAC GGC GGC GGC AAC GCC GAG
arg arg val thr val thr lys asp asp thr thr ile val asp gly gly gly asn ala glu
```

-continued

1021/341 1051/351
GAC GTC CAG GGC CGC GTC GCC CAG ATC AAG GCC GAG ATC GAG TCG ACC GAC TCG GAC TGG
asp val gln gly arg val ala gln ile lys ala glu ile glu ser thr asp ser asp trp 1081/361 1111/371
GAC CGC GAG AAG CTC CAG GAG CGC CTC GCC AAG CTG GCC GGC GGC GTC TGC GTG ATC CGC
asp arg glu lys leu gln glu arg leu ala lys leu ala gly gly val cys val ile arg 1141/381 1171/391
GTC GGC GCG GCC ACC GAG GTC GAG CTG AAG GAG CGC AAG CAC CGT CTG GAG GAC GCC ATC
val gly ala ala thr glu val glu leu lys glu arg lys his arg leu glu asp ala ile 1201/401 1231/411
TCC GCG ACC CGC GCC GCG GTC GAG GAG GGC ATC GTC TCC GGT GGT GGC TCC GCG CTG GTC
ser ala thr arg ala ala val glu glu gly ile val ser gly gly gly ser ala leu val 1261/421 1291/431
CAC GCC GTC AAG GTC CTG GAC GAC AAC CTC GGC CGC ACC GGC GAC GAG GCC ACC GGT GTC
his ala val lys val leu asp asp asn leu gly arg thr gly asp glu ala thr gly val and SEQ ID NO: 10:

1/1 31/11
ATG GCG AAG ATT CTG AAG TTC GAC GAG GAC GCC CGT CGC GCC CTT GAG CGC GGC GTG AAC
Met ala lys ile leu lys phe asp glu asp ala arg arg ala leu glu arg gly val asn 61/21 91/31
CAG CTG GCC GAC ACC GTC AAG GTG ACC ATC GGC CCC AAG GGC CGC AAC GTC GTC ATC GAC
gln leu ala asp thr val lys val thr ile gly pro lys gly arg asn val val ile asp 121/41 151/51
AAG AAG TTC GGC GCC CCG ACC ATC ACC AAC GAC GGC GTC ACC ATC GCC CGT GAG GTC GAG
lys lys phe gly ala pro thr ile thr asn asp gly val thr ile ala arg glu val glu 181/61 211/71
TGC GAC GAC CCG TAC GAG AAC CTC GGC GCC CAG CTC GTC AAG GAG GTG GCG ACC AAG ACC
cys asp asp pro tyr glu asn leu gly ala gln leu val lys glu val ala thr lys thr 241/81 271/91
AAC GAC ATC GCG GGT GAC GGC ACC ACC ACC GCG ACC GTG CTG GCC CAG GCG CTG GTC CGC
asn asp ile ala gly asp gly thr thr thr ala thr val leu ala gln ala leu val arg 301/101 331/111
GAG GGC CTG CGC AAC GTC GCC GCC GGC GCC TCC CCG GCC GCC CTG AAG AAG GGC ATC GAC
glu gly leu arg asn val ala ala gly ala ser pro ala ala leu lys lys gly ile asp 361/121 391/131
GCC GCC GTC GCC GCC GTC TCC GCC GAG CTG CTC GAC ACC GCG CGC CCG ATC GAC GAC AAG
ala ala val ala ala val ser ala glu leu leu asp thr ala arg pro ile asp asp lys 421/141 451/151
TCC GAC ATC GCC GCC GTC GCC GCG CTC TCC GCG CAG GAC AAG CAG GTC GGC GAG CTC ATC
ser asp ile ala ala val ala ala leu ser ala gln asp lys gln val gly glu leu ile 481/161 511/171
GCC GAG GCG ATG GAC AAG GTC GGC AAG GAC GGT GTC ATC ACC GTC GAG GAG TCC AAC ACC
ala glu ala met asp lys val gly lys asp gly val ile thr val glu glu ser asn thr 541/181 571/191
TTC GGT GTC GAC CTG GAC TTC ACC GAG GGC ATG GCC TTC GAC AAG GGC TAC CTG TCC CCG
phe gly val asp leu asp phe thr glu gly met ala phe asp lys gly tyr leu ser pro 601/201 631/211
TAC ATG GTG ACC GAC CAG GAG CGT ATG GAG GCC GTC CTC GAC GAC CCG TAC ATC CTG ATC
tyr met val thr asp gln glu arg met glu ala val leu asp asp pro tyr ile leu ile 661/221 691/231
CAC CAG GGC AAG ATC GGT TCG ATC CAG GAC CTG CTG CCG CTG CTG GAG AAG GTC ATC CAG
his gln gly lys ile gly ser ile gln asp leu leu pro leu leu glu lys val ile gln 721/241 751/251
GCG GGT GGC TCC AAG CCG CTG CTG ATC ATC GCC GAG GAC GTC GAG GGC GAG GCC CTG TCG
ala gly gly ser lys pro leu leu ile ile ala glu asp val glu gly glu ala leu ser 781/261 811/271
ACC CTG GTG GTC AAC AAG ATC CGC GGC ACG TTC AAC GCC GTC GCC GTC AAG GCG CCC GGC
thr leu val val asn lys ile arg gly thr phe asn ala val ala val lys ala pro gly -continued 841/281 871/291
TTC GGT GAC CGC CGC AAG GCG ATG CTC GGC GAC ATG GCC ACC CTC ACC GGT GCC ACC GTC
phe gly asp arg arg lys ala met leu gly asp met ala thr leu thr gly ala thr val 901/301 931/311
ATC GCC GAG GAG GTC GGC CTC AAG CTC GAC CAG GCC GGT CTG GAC GTG CTG GGC ACC GCC
ile ala glu glu val gly leu lys leu asp gln ala gly leu asp val leu gly thr ala 961/321 991/331
CGC CGC GTC ACC GTC ACC AAG GAC GAC ACG ACC ATC GTG GAC GGC GGC GGC AAC GCC GAG
arg arg val thr val thr lys asp asp thr thr ile val asp gly gly gly asn ala glu 1021/341 1051/351
GAC GTC CAG GGC CGC GTC GCC CAG ATC AAG GCC GAG ATC GAG TCG ACC GAC TCG GAC TGG
asp val gln gly arg val ala gln ile lys ala glu ile glu ser thr asp ser asp trp 1081/361 1111/371
GAC CGC GAG AAG CTC CAG GAG CGC CTC GCC AAG CTG GCC GGC GGC GTC TGC GTG ATC CGC
asp arg glu lys leu gln glu arg leu ala lys leu ala gly gly val cys val ile arg 1141/381 1171/391
GTC GGC GCG GCC ACC GAG GTC GAG CTG AAG GAG CGC AAG CAC CGT CTG GAG GAC GCC ATC
val gly ala ala thr glu val glu leu lys glu arg lys his arg leu glu asp ala ile 1201/401 1231/411
TCC GCG ACC CGC GCC GCG GTC GAG GAG GGC ATC GTC TCC GGT GGT GGC TCC GCG CTG GTC
ser ala thr arg ala ala val glu glu gly ile val ser gly gly gly ser ala leu val 1261/421 1291/431
CAC GCC GTC AAG GTC CTG GAC GAC AAC CTC GGC CGC ACC GGC GAC GAG GCC ACC GGT GTC
his ala val lys val leu asp asp asn leu gly arg thr gly asp glu ala thr gly val 1321/441 1351/451
GCG GTC GTC CGC CGC GCC GCC GTC GAG CCG CTG CGC TGG ATC GCC GAG AAC GCC GGC CTC
ala val val arg arg ala ala val glu pro leu arg trp ile ala glu asn ala gly leu 1381/461 1411/471
GAG GGC TAC GTC ATC ACC ACC AAG GTG GCG GAG CTC GAC AAG GGC CAG GGC TTC AAC GCG
glu gly tyr val ile thr thr lys val ala glu leu asp lys gly gln gly phe asn ala 1441/481 1471/491
GCC ACC GGC GAG TAC GGC GAC CTG GTC AAG GCC GGC GTC ATC GAC CCG GTC AAG GTC ACC
ala thr gly glu tyr gly asp leu val lys ala gly val ile asp pro val lys val thr 1501/501 1531/511
CGC TCC GCC CTG GAG AAC GCG GCC TCC ATC GCC TCC CTG CTC CTG ACG ACC GAG ACC CTG
arg ser ala leu glu asn ala ala ser ile ala ser leu leu leu thr thr glu thr leu 1561/521 1591/531
GTC GTC GAG AAG CCG GCC GAG GAG GAG CCC GAG GCC GGT CAC GGT CAC GGG CAC AGC CAC
val val glu lys pro ala glu glu glu pro glu ala gly his gly his gly his ser his .

6. The polypeptide according to claim 5, comprising an amino acid sequence which extends maximally from amino acid number 1 to amino acid number 170.

7. A nucleic acid sequence coding for a heat shock protein of claim 5 or 6.

8. The recombinant nucleotide sequence according to claim 1, wherein said regulatory sequence is present in Streptomyces.

9. A cell transformed by the expression vector according to claims 3 or 4, which recognizes said promoter and expresses said polypeptide.

10. A process for the production of a polypeptide comprising the steps of:

transforming a cell with the expression vector according to claims 3 or 4 under conditions which allow expression of said polypeptide, said cell being capable of recognizing said promoter; and recovering the polypeptide expressed.

11. The process according to claim 10, wherein said cell is of genus Mycobacterium.

12. An isolated nucleotide sequence selected from the following sequences:

P1 corresponding to one of the sequences (SEQ ID Nos: 2–3):

CATTGGCACTCCGCTTGACCGAGTGCTAATCGCGGTCATAGTCTCAGCTCTG
5' 3' or

GCATTGGCACTCCGCTTGACCGAGTGCTAATCGCGGTCATAGTCTCAGCTCTG
5' 3'

P2 corresponding to one of the sequences (SEQ ID Nos. 4–5):

GGAGGCCCCTAGCGCCTGCACTCTCCTACCCCGAGTGCTATTATTGGCGTTA
5' 3' or

GGAGGCCCCTAGCGCCTGCACTCTCCTACCCCGAGTGCTAATTATTGGCGTTA
5' 3'.

13. An 18 kD heat shock protein isolated from *Streptomyces albus* and having an isoelectric point higher than 9.

14. A cell of the genus Streptomyces transformed by the expression vector according to claims 3 or 4, which recognizes said promoter and expresses said polypeptide.

15. A process for the production of a polypeptide comprising the steps of:

transforming a cell of the genus Streptomyces by means of an expression vector according to claims 3 or 4 under conditions which allow expression of said polypeptide, said cell being capable of recognizing said promoter; and recovering the polypeptide expressed.

16. The process according to claim 15, wherein the conditions allowing the expression of said polypeptide include application of a heat shock.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GCACTCNNNN NNNNNGAGTG C 21

( 2 ) INFORMATION FOR SEQ ID NO:2:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

CATTGGCACT CCGCTTGACC GAGTGCTAAT CGCGGTCATA GTCTCAGCTC TG 52

( 2 ) INFORMATION FOR SEQ ID NO:3:

( i ) SEQUENCE CHARACTERISTICS:
( A ) LENGTH: 53 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

GCATTGGCAC TCCGCTTGAC CGAGTGCTAA TCGCGGTCAT AGTCTCAGCT CTG 53

( 2 ) INFORMATION FOR SEQ ID NO:4:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

GGAGGCCCCT AGCGCCTGCA CTCTCCTACC CCGAGTGCTA TTATTGGCGT TA 52

( 2 ) INFORMATION FOR SEQ ID NO:5:

( i ) SEQUENCE CHARACTERISTICS:
( A ) LENGTH: 53 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

GGAGGCCCCT AGCGCCTGCA CTCTCCTACC CCGAGTGCTA ATTATTGGCG TTA 53

(2) INFORMATION FOR SEQ ID NO:6:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

GCACTCNNNN NNNCCGAGTG CTAAT 25

(2) INFORMATION FOR SEQ ID NO:7:

(i) SEQUENCE CHARACTERISTICS:
(A) LENGTH: 309 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..306

(xi) SEQUENCE DESCRIPTION: SEQ ID NO:7:

```
GTG ACG ACC GCC AGC TCC AAG GTT GCC ATC AAG CCG CTC GAG GAC CGC      48
Val Thr Thr Ala Ser Ser Lys Val Ala Ile Lys Pro Leu Glu Asp Arg
  1               5                  10                  15

ATC GTG GTC CAG CCG CTC GAC GCC GAG CAG ACC ACG GCT TCG GGC CTG      96
Ile Val Val Gln Pro Leu Asp Ala Glu Gln Thr Thr Ala Ser Gly Leu
             20                  25                  30

GTC ATC CCG GAC ACC GCG AAG GAG AAG CCC CAG GAG GGC GTC GTC CTC     144
Val Ile Pro Asp Thr Ala Lys Glu Lys Pro Gln Glu Gly Val Val Leu
         35                  40                  45

GCG GTC GGC CCG GGC CGC TTC GAG AAC GGC GAG CGC CTG CCG CTC GAC     192
Ala Val Gly Pro Gly Arg Phe Glu Asn Gly Glu Arg Leu Pro Leu Asp
     50                  55                  60

GTC AAG ACC GGC GAC GTC GTG CTG TAC AGC AAG TAC GGC GGC ACC GAG     240
Val Lys Thr Gly Asp Val Val Leu Tyr Ser Lys Tyr Gly Gly Thr Glu
 65                  70                  75                  80

GTC AAG TAC AAC GGC GAG GAG TAC CTC GTC CTC TCG GCC CGC GAC GTT     288
Val Lys Tyr Asn Gly Glu Glu Tyr Leu Val Leu Ser Ala Arg Asp Val
                 85                  90                  95

CTC GCC ATC ATC GAG AAG TAG                                         309
Leu Ala Ile Ile Glu Lys
            100
```

(2) INFORMATION FOR SEQ ID NO:8:

(i) SEQUENCE CHARACTERISTICS:
(A) LENGTH: 1320 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..1320

(xi) SEQUENCE DESCRIPTION: SEQ ID NO:8:

```
ATG GCG AAG ATT CTG AAG TTC GAC GAG GAC GCC CGT CGC GCC CTT GAG      48
```

-continued

```
Met Ala Lys Ile Leu Lys Phe Asp Glu Asp Ala Arg Arg Ala Leu Glu
  1               5                  10                  15

 CGC GGC GTG AAC CAG CTG GCC GAC ACC GTC AAG GTG ACC ATC GGC CCC      96
Arg Gly Val Asn Gln Leu Ala Asp Thr Val Lys Val Thr Ile Gly Pro
             20                  25                  30

AAG GGC CGC AAC GTC GTC ATC GAC AAG AAG TTC GGC GCC CCG ACC ATC     144
Lys Gly Arg Asn Val Val Ile Asp Lys Lys Phe Gly Ala Pro Thr Ile
         35                  40                  45

ACC AAC GAC GGC GTC ACC ATC GCC CGT GAG GTC GAG TGC GAC GAC CCG     192
Thr Asn Asp Gly Val Thr Ile Ala Arg Glu Val Glu Cys Asp Asp Pro
     50                  55                  60

TAC GAG AAC CTC GGC GCC CAG CTC GTC AAG GAG GTG GCG ACC AAG ACC     240
Tyr Glu Asn Leu Gly Ala Gln Leu Val Lys Glu Val Ala Thr Lys Thr
 65                  70                  75                  80

AAC GAC ATC GCG GGT GAC GGC ACC ACC ACC GCG ACC GTG CTG GCC CAG     288
Asn Asp Ile Ala Gly Asp Gly Thr Thr Thr Ala Thr Val Leu Ala Gln
                 85                  90                  95

GCG CTG GTC CGC GAG GGC CTG CGC AAC GTC GCC GCC GGC GCC TCC CCG     336
Ala Leu Val Arg Glu Gly Leu Arg Asn Val Ala Ala Gly Ala Ser Pro
            100                 105                 110

GCC GCC CTG AAG AAG GGC ATC GAC GCC GCC GTC GCC GCC GTC TCC GCC     384
Ala Ala Leu Lys Lys Gly Ile Asp Ala Ala Val Ala Ala Val Ser Ala
        115                 120                 125

GAG CTG CTC GAC ACC GCG CGC CCG ATC GAC GAC AAG TCC GAC ATC GCC     432
Glu Leu Leu Asp Thr Ala Arg Pro Ile Asp Asp Lys Ser Asp Ile Ala
    130                 135                 140

GCC GTC GCC GCG CTC TCC GCG CAG GAC AAG CAG GTC GGC GAG CTC ATC     480
Ala Val Ala Ala Leu Ser Ala Gln Asp Lys Gln Val Gly Glu Leu Ile
145                 150                 155                 160

GCC GAG GCG ATG GAC AAG GTC GGC AAG GAC GGT GTC ATC ACC GTC GAG     528
Ala Glu Ala Met Asp Lys Val Gly Lys Asp Gly Val Ile Thr Val Glu
                165                 170                 175

GAG TCC AAC ACC TTC GGT GTC GAC CTG GAC TTC ACC GAG GGC ATG GCC     576
Glu Ser Asn Thr Phe Gly Val Asp Leu Asp Phe Thr Glu Gly Met Ala
            180                 185                 190

TTC GAC AAG GGC TAC CTG TCC CCG TAC ATG GTG ACC GAC CAG GAG CGT     624
Phe Asp Lys Gly Tyr Leu Ser Pro Tyr Met Val Thr Asp Gln Glu Arg
        195                 200                 205

ATG GAG GCC GTC CTC GAC GAC CCG TAC ATC CTG ATC CAC CAG GGC AAG     672
Met Glu Ala Val Leu Asp Asp Pro Tyr Ile Leu Ile His Gln Gly Lys
    210                 215                 220

ATC GGT TCG ATC CAG GAC CTG CTG CCG CTG CTG GAG AAG GTC ATC CAG     720
Ile Gly Ser Ile Gln Asp Leu Leu Pro Leu Leu Glu Lys Val Ile Gln
225                 230                 235                 240

GCG GGT GGC TCC AAG CCG CTG CTG ATC ATC GCC GAG GAC GTC GAG GGC     768
Ala Gly Gly Ser Lys Pro Leu Leu Ile Ile Ala Glu Asp Val Glu Gly
                245                 250                 255

GAG GCC CTG TCG ACC CTG GTG GTC AAC AAG ATC CGC GGC ACG TTC AAC     816
Glu Ala Leu Ser Thr Leu Val Val Asn Lys Ile Arg Gly Thr Phe Asn
            260                 265                 270

GCC GTC GCC GTC AAG GCG CCC GGC TTC GGT GAC CGC CGC AAG GCG ATG     864
Ala Val Ala Val Lys Ala Pro Gly Phe Gly Asp Arg Arg Lys Ala Met
        275                 280                 285

CTC GGC GAC ATG GCC ACC CTC ACC GGT GCC ACC GTC ATC GCC GAG GAG     912
Leu Gly Asp Met Ala Thr Leu Thr Gly Ala Thr Val Ile Ala Glu Glu
    290                 295                 300

GTC GGC CTC AAG CTC GAC CAG GCC GGT CTG GAC GTG CTG GGC ACC GCC     960
Val Gly Leu Lys Leu Asp Gln Ala Gly Leu Asp Val Leu Gly Thr Ala
305                 310                 315                 320

CGC CGC GTC ACC GTC ACC AAG GAC GAC ACG ACC ATC GTG GAC GGC GGC    1008
```

-continued

```
Arg Arg Val Thr Val Thr Lys Asp Asp Thr Thr Ile Val Asp Gly Gly
                325                     330                     335

GGC AAC GCC GAG GAC GTC CAG GGC CGC GTC GCC CAG ATC AAG GCC GAG        1056
Gly Asn Ala Glu Asp Val Gln Gly Arg Val Ala Gln Ile Lys Ala Glu
            340                     345                     350

ATC GAG TCG ACC GAC TCG GAC TGG GAC CGC GAG AAG CTC CAG GAG CGC        1104
Ile Glu Ser Thr Asp Ser Asp Trp Asp Arg Glu Lys Leu Gln Glu Arg
        355                     360                     365

CTC GCC AAG CTG GCC GGC GGC GTC TGC GTG ATC CGC GTC GGC GCG GCC        1152
Leu Ala Lys Leu Ala Gly Gly Val Cys Val Ile Arg Val Gly Ala Ala
    370                     375                     380

ACC GAG GTC GAG CTG AAG GAG CGC AAG CAC CGT CTG GAG GAC GCC ATC        1200
Thr Glu Val Glu Leu Lys Glu Arg Lys His Arg Leu Glu Asp Ala Ile
385                     390                     395                     400

TCC GCG ACC CGC GCC GCG GTC GAG GAG GGC ATC GTC TCC GGT GGT GGC        1248
Ser Ala Thr Arg Ala Ala Val Glu Glu Gly Ile Val Ser Gly Gly Gly
                405                     410                     415

TCC GCG CTG GTC CAC GCC GTC AAG GTC CTG GAC GAC AAC CTC GGC CGC        1296
Ser Ala Leu Val His Ala Val Lys Val Leu Asp Asp Asn Leu Gly Arg
            420                     425                     430

ACC GGC GAC GAG GCC ACC GGT GTC                                        1320
Thr Gly Asp Glu Ala Thr Gly Val
        435                     440
```

( 2 ) INFORMATION FOR SEQ ID NO:9:

( i ) SEQUENCE CHARACTERISTICS:
( A ) LENGTH: 2167 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

```
CCGGCCGGGC TGAGGTTGGC TGGCTGGCCG GGTTCGGCCG GTGGGTCGAG GTGGCCTGGC    60

CGGGCTCGCC AGGGTGAGTT GGCCGAGCCG AGGCGGCCCC GGGGCTCCCC GGGCCGAGTT   120

GCGCGGCCAG GCCAGGGCTC AGCAGGGTGG GGGAGTGGGG CAGGCGGCCC GGTAGGGGAG   180

TGCGGGAGGG CAGCGCGCGC CGCGCGCATT GGCACTCCGC TTGACCGAGT GCTAATCGCG   240

GTCATAGTCT CAGCTCTGGC ACTCCCCGCA GGAGAGTGCC AACACAGCGA CGGGCAGGTC   300

CCGGCACCCG CGACGACGGA TCGACCTGGT CGCCACACTC AGATCAGTTA ACCCCGTGAT   360

CTCCGAAGGG GGAGGTCGGA TCGTGACGAC CGCCAGCTCC AAGGTTGCCA TCAAGCCGCT   420

CGAGGACCGC ATCGTGGTCC AGCCGCTCGA CGCCGAGCAG ACCACGGCTT CGGGCCTGGT   480

CATCCCGGAC ACCGCGAAGG AGAAGCCCCA GGAGGGCGTC GTCCTCGCGG TCGGCCCGGG   540

CCGCTTCGAG AACGGCGAGC GCCTGCCGCT CGACGTCAAG ACCGGCGACG TCGTGCTGTA   600

CAGCAAGTAC GGCGGCACCG AGGTCAAGTA CAACGGCGAG GAGTACCTCG TCCTCTCGGC   660

CCGCGACGTT CTCGCCATCA TCGAGAAGTA GCAGGCCGGA GCGGTCCGGG CGCGAGCCCG   720

GACGGCAGAC TCCACCTTTT TCCTGAAGCG CGCCCCTGGC CCCCGCGAGT GTTTGCCGGG   780

TGGCGAGGGG CGCGTTTCAT TTCGAGAGCG CGGCGGCAGG CCGCTCCGAG AGGATTCGAA   840

AAGCTCCCAT GGCGAAGATT CTGAAGTTCG ACGAGGACGC CCGTCGCGCC CTTGAGCGCG   900

GCGTGAACCA GCTGGCCGAC ACCGTCAAGG TGACCATCGG CCCCAAGGGC CGCAACGTCG   960

TCATCGACAA GAAGTTCGGC GCCCCGACCA TCACCAACGA CGGCGTCACC ATCGCCCGTG  1020

AGGTCGAGTG CGACGACCCG TACGAGAACC TCGGCGCCCA GCTCGTCAAG GAGGTGGCGA  1080
```

-continued

CCAAGACCAA CGACATCGCG GGTGACGGCA CCACCACCGC GACCGTGCTG GCCCAGGCGC 1140

TGGTCCGCGA GGGCCTGCGC AACGTCGCCG CCGGCGCCTC CCCGGCCGCC CTGAAGAAGG 1200

GCATCGACGC CGCCGTCGCC GCCGTCTCCG CCGAGCTGCT CGACACCGCG CGCCCGATCG 1260

ACGACAAGTC CGACATCGCC GCCGTCGCCG CGCTCTCCGC GCAGGACAAG CAGGTCGGCG 1320

AGCTCATCGC CGAGGCGATG GACAAGGTCG GCAAGGACGG TGTCATCAAC GTCGAGGAGT 1380

CCAACACCTT CGGTGTCGAC CTGGACTTCA CCGAGGGCAT GGCCTTCGAC AAGGGCTACC 1440

TGTCCCCGTA CATGGTGACC GACCAGGAGC GTATGGAGGC CGTCCTCGAC GACCCGTACA 1500

TCCTGATCCA CCAGGGCAAG ATCGGTTCGA TCCAGGACCT GCTGCCGCTG CTGGAGAAGG 1560

TCATCCAGGC GGGTGGCTCC AAGCCGCTGC TGATCATCGC CGAGGACGTC GAGGGCGAGG 1620

CCCTGTCGAC CCTGGTGGTC AACAAGATCC GCGGCACGTT CAACGCCGTC GCCGTCAAGG 1680

CGCCCGGCTT CGGTGACCGC CGCAAGGCGA TGCTCGGCGA CATGGCCACC CTCACCGGTG 1740

CCACCGTCAT CGCCGAGGAG GTCGGCCTCA AGCTCGACCA GGCCGGTCTG GACGTGCTGG 1800

GCACCGCCCG CCGCGTCACC GTCACCAAGG ACGACACGAC CATCGTGGAC CTGGAGAAGG 1860

ACGCCGAGGA CGTCCAGGGC CGCGTCGCCC AGATCAAGGC CGAGATCGAG TCGACCGACT 1920

CGGACTGGGA CCGCGAGAAG CTCCAGGAGC GCCTCGCCAA GCTGGCCGGC GGCGTCTGCG 1980

TGATCCGCGT CGGCGCGGCC ACCGAGGTCG AGCTGAAGGA GCGCAAGCAC CGTCTGGAGG 2040

ACGCCATCTC CGCGACCCGC GCCGCGGTCG AGGAGGGCAT CGTCTCCGGT GGTGGCTCCG 2100

CGCTGGTCCA CGCCGTCAAG GTCCTGGACG ACAACCTCGG CCGCACCGGC GACGAGGCCA 2160

CCGGTGT 2167

( 2 ) INFORMATION FOR SEQ ID NO:10:

( i ) SEQUENCE CHARACTERISTICS:
( A ) LENGTH: 1620 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..1620

( x i ) SEQUENCE DESCRIPTION: SEQ ID NO:10:

ATG GCG AAG ATT CTG AAG TTC GAC GAG GAC GCC CGT CGC GCC CTT GAG 48
Met Ala Lys Ile Leu Lys Phe Asp Glu Asp Ala Arg Arg Ala Leu Glu
1 5 10 15

CGC GGC GTG AAC CAG CTG GCC GAC ACC GTC AAG GTG ACC ATC GGC CCC 96
Arg Gly Val Asn Gln Leu Ala Asp Thr Val Lys Val Thr Ile Gly Pro
20 25 30

AAG GGC CGC AAC GTC GTC ATC GAC AAG AAG TTC GGC GCC CCG ACC ATC 144
Lys Gly Arg Asn Val Val Ile Asp Lys Lys Phe Gly Ala Pro Thr Ile
35 40 45

ACC AAC GAC GGC GTC ACC ATC GCC CGT GAG GTC GAG TGC GAC GAC CCG 192
Thr Asn Asp Gly Val Thr Ile Ala Arg Glu Val Glu Cys Asp Asp Pro
50 55 60

TAC GAG AAC CTC GGC GCC CAG CTC GTC AAG GAG GTG GCG ACC AAG ACC 240
Tyr Glu Asn Leu Gly Ala Gln Leu Val Lys Glu Val Ala Thr Lys Thr
65 70 75 80

AAC GAC ATC GCG GGT GAC GGC ACC ACC ACC GCG ACC GTG CTG GCC CAG 288
Asn Asp Ile Ala Gly Asp Gly Thr Thr Thr Ala Thr Val Leu Ala Gln
85 90 95

GCG CTG GTC CGC GAG GGC CTG CGC AAC GTC GCC GCC GGC GCC TCC CCG 336

-continued

```
Ala Leu Val Arg Glu Gly Leu Arg Asn Val Ala Ala Gly Ala Ser Pro
            100                 105                 110

GCC GCC CTG AAG AAG GGC ATC GAC GCC GCC GTC GCC GCC GTC TCC GCC     384
Ala Ala Leu Lys Lys Gly Ile Asp Ala Ala Val Ala Ala Val Ser Ala
        115                 120                 125

GAG CTG CTC GAC ACC GCG CGC CCG ATC GAC GAC AAG TCC GAC ATC GCC     432
Glu Leu Leu Asp Thr Ala Arg Pro Ile Asp Asp Lys Ser Asp Ile Ala
    130                 135                 140

GCC GTC GCC GCG CTC TCC GCG CAG GAC AAG CAG GTC GGC GAG CTC ATC     480
Ala Val Ala Ala Leu Ser Ala Gln Asp Lys Gln Val Gly Glu Leu Ile
145                 150                 155                 160

GCC GAG GCG ATG GAC AAG GTC GGC AAG GAC GGT GTC ATC ACC GTC GAG     528
Ala Glu Ala Met Asp Lys Val Gly Lys Asp Gly Val Ile Thr Val Glu
                165                 170                 175

GAG TCC AAC ACC TTC GGT GTC GAC CTG GAC TTC ACC GAG GGC ATG GCC     576
Glu Ser Asn Thr Phe Gly Val Asp Leu Asp Phe Thr Glu Gly Met Ala
            180                 185                 190

TTC GAC AAG GGC TAC CTG TCC CCG TAC ATG GTG ACC GAC CAG GAG CGT     624
Phe Asp Lys Gly Tyr Leu Ser Pro Tyr Met Val Thr Asp Gln Glu Arg
        195                 200                 205

ATG GAG GCC GTC CTC GAC GAC CCG TAC ATC CTG ATC CAC CAG GGC AAG     672
Met Glu Ala Val Leu Asp Asp Pro Tyr Ile Leu Ile His Gln Gly Lys
    210                 215                 220

ATC GGT TCG ATC CAG GAC CTG CTG CCG CTG CTG GAG AAG GTC ATC CAG     720
Ile Gly Ser Ile Gln Asp Leu Leu Pro Leu Leu Glu Lys Val Ile Gln
225                 230                 235                 240

GCG GGT GGC TCC AAG CCG CTG CTG ATC ATC GCC GAG GAC GTC GAG GGC     768
Ala Gly Gly Ser Lys Pro Leu Leu Ile Ile Ala Glu Asp Val Glu Gly
                245                 250                 255

GAG GCC CTG TCG ACC CTG GTG GTC AAC AAG ATC CGC GGC ACG TTC AAC     816
Glu Ala Leu Ser Thr Leu Val Val Asn Lys Ile Arg Gly Thr Phe Asn
            260                 265                 270

GCC GTC GCC GTC AAG GCG CCC GGC TTC GGT GAC CGC CGC AAG GCG ATG     864
Ala Val Ala Val Lys Ala Pro Gly Phe Gly Asp Arg Arg Lys Ala Met
        275                 280                 285

CTC GGC GAC ATG GCC ACC CTC ACC GGT GCC ACC GTC ATC GCC GAG GAG     912
Leu Gly Asp Met Ala Thr Leu Thr Gly Ala Thr Val Ile Ala Glu Glu
    290                 295                 300

GTC GGC CTC AAG CTC GAC CAG GCC GGT CTG GAC GTG CTG GGC ACC GCC     960
Val Gly Leu Lys Leu Asp Gln Ala Gly Leu Asp Val Leu Gly Thr Ala
305                 310                 315                 320

CGC CGC GTC ACC GTC ACC AAG GAC GAC ACG ACC ATC GTG GAC GGC GGC    1008
Arg Arg Val Thr Val Thr Lys Asp Asp Thr Thr Ile Val Asp Gly Gly
                325                 330                 335

GGC AAC GCC GAG GAC GTC CAG GGC CGC GTC GCC CAG ATC AAG GCC GAG    1056
Gly Asn Ala Glu Asp Val Gln Gly Arg Val Ala Gln Ile Lys Ala Glu
            340                 345                 350

ATC GAG TCG ACC GAC TCG GAC TGG GAC CGC GAG AAG CTC CAG GAG CGC    1104
Ile Glu Ser Thr Asp Ser Asp Trp Asp Arg Glu Lys Leu Gln Glu Arg
        355                 360                 365

CTC GCC AAG CTG GCC GGC GGC GTC TGC GTG ATC CGC GTC GGC GCG GCC    1152
Leu Ala Lys Leu Ala Gly Gly Val Cys Val Ile Arg Val Gly Ala Ala
    370                 375                 380

ACC GAG GTC GAG CTG AAG GAG CGC AAG CAC CGT CTG GAG GAC GCC ATC    1200
Thr Glu Val Glu Leu Lys Glu Arg Lys His Arg Leu Glu Asp Ala Ile
385                 390                 395                 400

TCC GCG ACC CGC GCC GCG GTC GAG GAG GGC ATC GTC TCC GGT GGT GGC    1248
Ser Ala Thr Arg Ala Ala Val Glu Glu Gly Ile Val Ser Gly Gly Gly
                405                 410                 415

TCC GCG CTG GTC CAC GCC GTC AAG GTC CTG GAC GAC AAC CTC GGC CGC    1296
```

-continued

```
Ser Ala Leu Val His Ala Val Lys Val Leu Asp Asp Asn Leu Gly Arg
            420                 425                 430

ACC GGC GAC GAG GCC ACC GGT GTC GCG GTC GTC CGC CGC GCC GCC GTC   1344
Thr Gly Asp Glu Ala Thr Gly Val Ala Val Val Arg Arg Ala Ala Val
        435                 440                 445

GAG CCG CTG CGC TGG ATC GCC GAG AAC GCC GGC CTC GAG GGC TAC GTC   1392
Glu Pro Leu Arg Trp Ile Ala Glu Asn Ala Gly Leu Glu Gly Tyr Val
    450                 455                 460

ATC ACC ACC AAG GTG GCG GAG CTC GAC AAG GGC CAG GGC TTC AAC GCG   1440
Ile Thr Thr Lys Val Ala Glu Leu Asp Lys Gly Gln Gly Phe Asn Ala
465                 470                 475                 480

GCC ACC GGC GAG TAC GGC GAC CTG GTC AAG GCC GGC GTC ATC GAC CCG   1488
Ala Thr Gly Glu Tyr Gly Asp Leu Val Lys Ala Gly Val Ile Asp Pro
                485                 490                 495

GTC AAG GTC ACC GCG TCC GCC CTG GAG AAC GCG GCC TCC ATC GCC TCC   1536
Val Lys Val Thr Ala Ser Ala Leu Glu Asn Ala Ala Ser Ile Ala Ser
            500                 505                 510

CTG CTC CTG ACG ACC GAG ACC CTG GTC GTC GAG AAG CCG GCC GAG GAG   1584
Leu Leu Leu Thr Thr Glu Thr Leu Val Val Glu Lys Pro Ala Glu Glu
        515                 520                 525

GAG CCC GAG GCC GGT CAC GGT CAC GGG CAC AGC CAC                   1620
Glu Pro Glu Ala Gly His Gly His Gly His Ser His
    530                 535                 540
```

( 2 ) INFORMATION FOR SEQ ID NO:11:

( i ) SEQUENCE CHARACTERISTICS:
( A ) LENGTH: 2668 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

```
CCGGCCGGGC TGAGGTTGGC TGGCTGGCCG GGTTCGGCCG GTGGGTCGAG GTGGCCTGGC     60
CGGGCTCGCC AGGGTGAGTT GGCCGAGCCG AGGCGGCCCC GGGGCTCCCC GGGCCGAGTT    120
GGCGCGGCCA GGCCAGGGCT CAGCAGGGTG GGGGAGTGGG GCAGGCGGCC CGGTAGGGGA    180
GTGCGGGAGG GCAGCGCGCG CCGCGCGCAT TGGCACTCCG CTTGACCGAG TGCTAATCGC    240
GGTCATAGTC TCAGCTCTGG CACTCCCCGC AGGAGACTGC CAACACAGCG ACGGGCAGGT    300
CCGGCACCCG CGACGACGGA TCGACCTGGT CGCCACACTC AGATCAGTTA ACCCCGTGAT    360
CTCCGAAGGG GGAGGTCGGA TCGTGACGAC CGCCAGCTCC AAGGTTGCCA TCAAGCCGCT    420
CGAGGACCGC ATCGTGGTCC AGCCGCTCGA CGCCGAGCAG ACCACGGCTT CGGGCCTGGT    480
CATCCCGGAC ACCGCGAAGG AGAAGCCCCA GGAGGGCGTC GTCCTCGCGG TCGGCCCGGG    540
CCGCTTCGAG AACGGCGAGC GCCTGCCGCT CGACGTCAAG ACCGGCGACG TCGTGCTGTA    600
CAGCAAGTAC GGCGGCACCG AGGTCAAGTA CAACGGCGAG GAGTACCTCG TCCTCTCGGC    660
CCGCGACGTT CTCGCCATCA TCGAGAAGTA GCAGGCCGGA GCGGTCCGGG CGCGAGCCCG    720
GACGGCAGAC TCCACCTTTT TCCTGAAGCG CGCCCCTGGC CCCCGCGAGT GTTTGCCGGG    780
TGGCGAGGGG CGCGTTTCAT TTCGAGAGCG CGGCGGCAGG CCGCTCCGAG AGGATTCGAA    840
AAGCTCCCAT GGCGAAGATT CTGAAGTTCG ACGAGGACGC CCGTCGCGCC CTTGAGCGCG    900
GCGTGAACCA GCTGGCCGAC ACCGTCAAGG TGACCATCGG CCCCAAGGGC CGCAACGTCG    960
TCATCGACAA GAAGTTCGGC GCCCCGACCA TCACCAACGA CGGCGTCACC ATCGCCCGTG   1020
AGGTCGAGTG CGACGACCCG TACGAGAACC TCGGCGCCCA GCTCGTCAAG GAGGTGGCGA   1080
```

-continued

| | | | | | | |
|---|---|---|---|---|---|---|
| CCAAGACCAA | CGACATCGCG | GGTGACGGCA | CCACCACCGC | GACCGTGCTG | GCCCAGGCGC | 1140 |
| TGGTCCGCGA | GGGCCTGCGC | AACGTCGCCG | CCGGCGCCTC | CCCGGCCGCC | CTGAAGAAGG | 1200 |
| GCATCGACGC | CGCCGTCGCC | GCCGTCTCCG | CCGAGCTGCT | CGACACCGCG | CGCCCGATCG | 1260 |
| ACGACAAGTC | CGACATCGCC | GCCGTCGCCG | CGCTCTCCGC | GCAGGACAAG | CAGGTCGGCG | 1320 |
| AGCTCATCGC | CGAGGCGATG | GACAAGGTCG | GCAAGGACGG | TGTCATCAAC | GTCGAGGAGT | 1380 |
| CCAACACCTT | CGGTGTCGAC | CTGGACTTCA | CCGAGGGCAT | GGCCTTCGAC | AAGGGCTACC | 1440 |
| TGTCCCCGTA | CATGGTGACC | GACCAGGAGC | GTATGGAGGC | CGTCCTCGAC | GACCCGTACA | 1500 |
| TCCTGATCCA | CCAGGGCAAG | ATCGGTTCGA | TCCAGGACCT | GCTGCCGCTG | CTGGAGAAGG | 1560 |
| TCATCCAGGC | GGGTGGCTCC | AAGCCGCTGC | TGATCATCGC | CGAGGACGTC | GAGGGCGAGG | 1620 |
| CCCTGTCGAC | CCTGGTGGTC | AACAAGATCC | GCGGCACGTT | CAACGCCGTC | GCCGTCAAGG | 1680 |
| CGCCCGGCTT | CGGTGACCGC | CGCAAGGCGA | TGCTCGGCGA | CATGGCCACC | CTCACCGGTG | 1740 |
| CCACCGTCAT | CGCCGAGGAG | GTCGGCCTCA | AGCTCGACCA | GGCCGGTCTG | GACGTGCTGG | 1800 |
| GCACCGCCCG | CCGCGTCACC | GTCACCAAGG | ACGACACGAC | CATCGTGGAC | CTGGAGAAGG | 1860 |
| ACGCCGAGGA | CGTCCAGGGC | CGCGTCGCCC | AGATCAAGGC | CGAGATCGAG | TCGACCGACT | 1920 |
| CGGACTGGGA | CCGCGAGAAG | CTCCAGGAGC | GCCTCGCCAA | GCTGGCCGGC | GGCGTCTGCG | 1980 |
| TGATCCGCGT | CGGCGCGGCC | ACCGAGGTCG | AGCTGAAGGA | GCGCAAGCAC | CGTCTGGAGG | 2040 |
| ACGCCATCTC | CGCGACCCGC | GCCGCGGTCG | AGGAGGGCAT | CGTCTCCGGT | GGTGGCTCCG | 2100 |
| CGCTGGTCCA | CGCCGTCAAG | GTCCTGGACG | ACAACCTCGG | CCGCACCGGC | GACGAGGCCA | 2160 |
| CCGGTGTCGC | GGTCGTCCGC | CGCGCCGCCG | TCGAGCCGCT | GCGCTGGATC | GCCGAGAACG | 2220 |
| CCGGCCTCGA | GGGCTACGTC | ATCACCACCA | AGGTGGCGGA | GCTCGACAAG | GGCCAGGGCT | 2280 |
| TCAACGCGGC | CACCGGCGAG | TACGGCGACC | TGGTCAAGGC | CGGCGTCATC | GACCCGGTCA | 2340 |
| AGGTCACCCG | CTCCGCCCTG | GAGAACGCGG | CCTCCATCGC | CTCCCTGCTC | CTGACGACCG | 2400 |
| AGACCCTGGT | CGTCGAGAAG | CCGGCCGAGG | AGGAGCCCGA | GGCCGGTCAC | GGTCACGGGC | 2460 |
| ACAGCCACTG | AGGCTGACCC | CTTCCGCAGC | CGAGGCCCGG | CTCCCCGTCG | CGGGGAGCCG | 2520 |
| GGCCTCCGGC | GTGTCCGGGA | CCCCCCGGGA | CGCGCGACGC | CTACCGCGGC | CCGTACTTGC | 2580 |
| GGCCGGTACG | CGAGGTCATC | CCGGTCAGCA | GGGCCCGCGG | GGTCAGCTTC | ACCAGGCCCA | 2640 |
| TCAGCGCCTT | GTACCGAGGG | TCCGGGAT | | | | 2668 |

( 2 ) INFORMATION FOR SEQ ID NO:12:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

Asp Asp Pro Tyr Glu Asn Leu Gly Ala Gln
1 5 10

( 2 ) INFORMATION FOR SEQ ID NO:13:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

-continued ( i x ) FEATURE:
( A ) NAME/KEY: misc_feature
( B ) LOCATION: 9
( D ) OTHER INFORMATION: /note= "Nucleotide 9 wherein S is C or G."

( i x ) FEATURE:
( A ) NAME/KEY: misc_feature
( B ) LOCATION: 21
( D ) OTHER INFORMATION: /note= "Nucleotide 21 wherein S is C or G."

( i x ) FEATURE:
( A ) NAME/KEY: misc_feature
( B ) LOCATION: 27
( D ) OTHER INFORMATION: /note= "Nucleotide 27 wherein Y is C or T."

( x i ) SEQUENCE DESCRIPTION: SEQ ID NO:13:

GACGACCCST ACGAGAACCT SGGCGCYCA 29

( 2 ) INFORMATION FOR SEQ ID NO:14:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 9
( D ) OTHER INFORMATION: /note= "Nucleotide 9 wherein S is C or G."

( i x ) FEATURE:
( A ) NAME/KEY: misc_feature
( B ) LOCATION: 21
( D ) OTHER INFORMATION: /note= "Nucleotide 21 wherein S is C or G."

( i x ) FEATURE:
( A ) NAME/KEY: misc_feature
( B ) LOCATION: 27
( D ) OTHER INFORMATION: /note= "Nucleotide 27 wherein R is G or A."

( x i ) SEQUENCE DESCRIPTION: SEQ ID NO:14:

CTGCTGGGSA TGCTCTTGGA SCCGCGRGTC 30

( 2 ) INFORMATION FOR SEQ ID NO:15:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

Gly His Gly His Gly His Ser His
1 5